(12) United States Patent
Byers et al.

(10) Patent No.: US 8,388,521 B2
(45) Date of Patent: Mar. 5, 2013

(54) INTEGRATED LOCKING DEVICE WITH ACTIVE SEALING

(75) Inventors: Ransom H. Byers, Mountain View, CA (US); Alexander E. Dillon, Cambridge, MA (US); Thomas C. Kochem, Belmont, MA (US); Daniel W. Rice, Gettysburg, PA (US); Allison L. Schmidt, Dothan, AL (US); James M. Weldon, Newton, MA (US); Gary A. Jordan, Litchfield, NH (US); Christopher S. Mauhar, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 840 days.

(21) Appl. No.: 12/467,971

(22) Filed: May 18, 2009

(65) Prior Publication Data

US 2010/0081878 A1 Apr. 1, 2010

Related U.S. Application Data

(60) Provisional application No. 61/054,393, filed on May 19, 2008.

(51) Int. Cl.
*A61B 1/00* (2006.01)
*A61B 1/12* (2006.01)
(52) U.S. Cl. ............... 600/154; 600/159; 604/167.04
(58) Field of Classification Search .......... 600/154, 600/159; 604/167.01–167.06, 256
See application file for complete search history.

(56) References Cited

U.S. PATENT DOCUMENTS

| 561,059 | A | 5/1896 | Mitchell et al. |
|---|---|---|---|
| 1,204,053 | A | 11/1916 | Moore |
| 1,213,001 | A | 1/1917 | Philips |
| 1,901,731 | A | 3/1933 | Buerger |
| 2,623,520 | A | 12/1952 | Bamford, Jr. et al. |
| 3,015,869 | A | 1/1962 | Rapata |
| 3,536,281 | A | 10/1970 | Meehan et al. |
| 3,602,228 | A | 8/1971 | Cowley |
| 3,677,243 | A | 7/1972 | Nerz |
| 4,178,920 | A | 12/1979 | Cawood, Jr. et al. |
| 4,198,958 | A | 4/1980 | Utsugi |

(Continued)

FOREIGN PATENT DOCUMENTS

| DE | 41 15 007 A1 | 11/1992 |
|---|---|---|
| DE | 199 11 911 A1 | 9/1999 |

(Continued)

OTHER PUBLICATIONS

Arndorfer Inc. Information Sheet, dated on or before Mar. 6, 2000, 7 sheets.

(Continued)

*Primary Examiner* — Anhtuan Nguyen
*Assistant Examiner* — Arnaldo Torres Diaz
(74) *Attorney, Agent, or Firm* — Seager Tufte & Wickhem LLC

(57) ABSTRACT

Endoscope assemblies, biopsy caps, and methods for making and using the same. An example endoscope assembly may include an endoscope having a channel formed therein and a port that provides access to the channel. A cap may be coupled to the port. The cap may include a base and an outer shell. A locking member may be coupled to the outer shell. An inner seal member may be disposed within the outer shell. One or more openings may extend through the cap and into the channel. An actuator may be coupled to the base for shifting the inner seal member between an unsealed configuration and a sealed configuration.

3 Claims, 32 Drawing Sheets

U.S. PATENT DOCUMENTS

| | | | |
|---|---|---|---|
| 4,306,562 A | 12/1981 | Osborne | |
| 4,326,516 A | 4/1982 | Schultz et al. | |
| 4,345,606 A | 8/1982 | Littleford | |
| 4,367,905 A | 1/1983 | Nauta | |
| 4,411,654 A | 10/1983 | Boarini et al. | |
| 4,412,832 A | 11/1983 | Kling et al. | |
| 4,474,174 A | 10/1984 | Petruzzi | |
| RE31,855 E | 3/1985 | Osborne | |
| 4,509,944 A | 4/1985 | King et al. | |
| 4,609,370 A | 9/1986 | Morrison | |
| 4,653,477 A | 3/1987 | Akui et al. | |
| 4,687,470 A | 8/1987 | Okada | |
| 4,696,668 A | 9/1987 | Wilcox | |
| 4,700,694 A | 10/1987 | Shishido | |
| 4,715,360 A | 12/1987 | Akui et al. | |
| 4,723,942 A | 2/1988 | Scott | |
| 4,738,666 A | 4/1988 | Fuqua | |
| 4,748,982 A | 6/1988 | Horzewski et al. | |
| 4,762,129 A | 8/1988 | Bonzel | |
| 4,771,777 A | 9/1988 | Horzewski et al. | |
| 4,781,677 A | 11/1988 | Wilcox | |
| 4,787,884 A | 11/1988 | Goldberg | |
| D301,365 S | 5/1989 | Gette | |
| 4,835,824 A | 6/1989 | Durham et al. | |
| 4,844,092 A | 7/1989 | Rydell et al. | |
| 4,858,810 A | 8/1989 | Intlekofer et al. | |
| 4,867,605 A | 9/1989 | Myers et al. | |
| 4,900,184 A | 2/1990 | Cleveland | |
| 4,905,667 A | 3/1990 | Foerster et al. | |
| 4,909,798 A * | 3/1990 | Fleischhacker et al. | 604/256 |
| 4,917,103 A | 4/1990 | Gambale et al. | |
| 4,920,953 A | 5/1990 | McGown | |
| 4,927,418 A | 5/1990 | Dake et al. | |
| 4,928,669 A | 5/1990 | Sullivan | |
| 4,928,693 A | 5/1990 | Goodin et al. | |
| 4,932,413 A | 6/1990 | Shockey et al. | |
| 4,940,062 A | 7/1990 | Hampton et al. | |
| 4,946,443 A | 8/1990 | Hauser et al. | |
| 4,973,329 A | 11/1990 | Park et al. | |
| 4,983,168 A | 1/1991 | Moorehead | |
| 4,988,356 A | 1/1991 | Crittenden et al. | |
| 4,995,872 A | 2/1991 | Ferrara | |
| 4,997,421 A | 3/1991 | Palsrok et al. | |
| 5,026,366 A | 6/1991 | Leckrone | |
| 5,034,001 A | 7/1991 | Garrison et al. | |
| 5,040,548 A | 8/1991 | Yock | |
| 5,061,273 A | 10/1991 | Yock | |
| 5,064,414 A | 11/1991 | Revane | |
| 5,098,064 A | 3/1992 | Daly et al. | |
| 5,106,054 A | 4/1992 | Mollenauer et al. | |
| 5,125,915 A | 6/1992 | Berry et al. | |
| 5,127,393 A | 7/1992 | McFarlin et al. | |
| 5,127,626 A | 7/1992 | Hilal et al. | |
| 5,135,535 A | 8/1992 | Kramer | |
| 5,137,288 A | 8/1992 | Starkey et al. | |
| 5,137,517 A | 8/1992 | Loney et al. | |
| 5,139,032 A | 8/1992 | Jahrmarkt et al. | |
| 5,147,377 A | 9/1992 | Sahota | |
| 5,154,725 A | 10/1992 | Leopold | |
| 5,158,545 A | 10/1992 | Trudell et al. | |
| 5,160,323 A | 11/1992 | Andrew | |
| 5,161,534 A | 11/1992 | Berthiaume | |
| 5,163,941 A | 11/1992 | Garth et al. | |
| 5,167,634 A | 12/1992 | Corrigan, Jr. et al. | |
| 5,167,636 A * | 12/1992 | Clement | 604/167.03 |
| 5,171,222 A | 12/1992 | Euteneuer et al. | |
| 5,180,367 A | 1/1993 | Kontos et al. | |
| 5,191,888 A | 3/1993 | Palmer et al. | |
| 5,195,978 A | 3/1993 | Schiffer | |
| 5,199,948 A | 4/1993 | McPhee | |
| 5,205,822 A | 4/1993 | Johnson et al. | |
| 5,219,332 A | 6/1993 | Nelson et al. | |
| 5,219,335 A | 6/1993 | Willard et al. | |
| 5,232,445 A | 8/1993 | Bonzel | |
| 5,248,306 A | 9/1993 | Clark et al. | |
| 5,250,033 A | 10/1993 | Evans et al. | |
| 5,263,932 A | 11/1993 | Jang | |
| 5,267,958 A | 12/1993 | Buchbinder et al. | |
| 5,279,562 A | 1/1994 | Sirhan et al. | |
| 5,281,203 A | 1/1994 | Ressemann | |
| 5,282,479 A | 2/1994 | Havran | |
| 5,290,232 A | 3/1994 | Johnson et al. | |
| 5,290,241 A | 3/1994 | Kraus et al. | |
| 5,300,085 A | 4/1994 | Yock | |
| 5,304,143 A | 4/1994 | Green et al. | |
| 5,306,247 A | 4/1994 | Pfenninger | |
| 5,308,318 A | 5/1994 | Plassche, Jr. | |
| 5,314,408 A | 5/1994 | Salmon et al. | |
| 5,320,602 A | 6/1994 | Karpiel | |
| 5,324,259 A | 6/1994 | Taylor et al. | |
| 5,324,269 A | 6/1994 | Miraki | |
| 5,328,472 A | 7/1994 | Steinke et al. | |
| 5,334,143 A | 8/1994 | Carroll | |
| 5,334,147 A | 8/1994 | Johnson | |
| 5,334,187 A | 8/1994 | Fischell et al. | |
| 5,336,184 A | 8/1994 | Teirstein | |
| 5,338,313 A | 8/1994 | Mollenauer et al. | |
| 5,342,297 A | 8/1994 | Jang | |
| 5,346,498 A | 9/1994 | Greelis et al. | |
| 5,350,395 A | 9/1994 | Yock | |
| 5,352,215 A | 10/1994 | Thome et al. | |
| 5,354,280 A | 10/1994 | Haber et al. | |
| 5,357,978 A | 10/1994 | Turk | |
| 5,364,355 A | 11/1994 | Alden et al. | |
| 5,364,376 A | 11/1994 | Horzewski et al. | |
| 5,368,567 A | 11/1994 | Lee | |
| 5,370,623 A | 12/1994 | Kreamer | |
| 5,380,283 A | 1/1995 | Johnson | |
| 5,385,552 A | 1/1995 | Haber et al. | |
| 5,387,226 A | 2/1995 | Miraki | |
| 5,389,087 A | 2/1995 | Miraki | |
| 5,389,100 A | 2/1995 | Bacich et al. | |
| 5,391,153 A | 2/1995 | Haber et al. | |
| 5,395,335 A | 3/1995 | Jang | |
| 5,395,342 A | 3/1995 | Yoon | |
| 5,397,302 A | 3/1995 | Weaver et al. | |
| 5,397,335 A | 3/1995 | Gresl et al. | |
| 5,407,433 A * | 4/1995 | Loomas | 604/167.06 |
| 5,409,459 A | 4/1995 | Gambale | |
| 5,413,559 A | 5/1995 | Sirhan et al. | |
| 5,415,633 A | 5/1995 | Lazarus et al. | |
| 5,415,639 A | 5/1995 | VandenEinde et al. | |
| 5,441,486 A | 8/1995 | Yoon | |
| 5,448,993 A | 9/1995 | Lynch et al. | |
| 5,449,363 A | 9/1995 | Brust et al. | |
| 5,451,233 A | 9/1995 | Yock | |
| 5,454,790 A | 10/1995 | Dubrul | |
| 5,458,584 A | 10/1995 | Ginn et al. | |
| 5,458,605 A | 10/1995 | Klemm | |
| 5,460,168 A | 10/1995 | Masubuchi et al. | |
| 5,462,530 A | 10/1995 | Jang | |
| 5,480,389 A | 1/1996 | McWha et al. | |
| 5,489,271 A | 2/1996 | Andersen | |
| 5,490,837 A | 2/1996 | Blaeser et al. | |
| 5,490,859 A | 2/1996 | Mische et al. | |
| 5,496,346 A | 3/1996 | Horzewski et al. | |
| 5,501,227 A | 3/1996 | Yock | |
| 5,531,700 A | 7/1996 | Moore et al. | |
| 5,536,234 A | 7/1996 | Newman | |
| 5,536,248 A | 7/1996 | Weaver et al. | |
| 5,540,236 A | 7/1996 | Ginn | |
| 5,547,469 A | 8/1996 | Rowland et al. | |
| 5,599,299 A | 2/1997 | Weaver et al. | |
| 5,599,300 A | 2/1997 | Weaver et al. | |
| 5,605,162 A | 2/1997 | Mirzaee et al. | |
| 5,613,949 A | 3/1997 | Miraki | |
| 5,626,600 A | 5/1997 | Horzewski et al. | |
| 5,634,475 A | 6/1997 | Wolvek | |
| 5,637,086 A | 6/1997 | Ferguson et al. | |
| 5,645,519 A | 7/1997 | Lee et al. | |
| 5,685,853 A | 11/1997 | Bonnet | |
| 5,693,015 A | 12/1997 | Walker et al. | |
| 5,706,827 A | 1/1998 | Ehr et al. | |
| 5,707,363 A | 1/1998 | Crawford et al. | |
| 5,709,658 A | 1/1998 | Sirhan et al. | |
| 5,718,680 A | 2/1998 | Kraus et al. | |
| 5,725,504 A | 3/1998 | Collins | |

| | | |
|---|---|---|
| 5,755,695 A | 5/1998 | Erickson et al. |
| 5,765,682 A | 6/1998 | Bley et al. |
| 5,788,681 A | 8/1998 | Weaver et al. |
| 5,800,414 A | 9/1998 | Cazal |
| 5,820,600 A | 10/1998 | Carlson et al. |
| 5,823,995 A | 10/1998 | Fitzmaurice et al. |
| 5,833,706 A | 11/1998 | St. Germain et al. |
| 5,836,306 A | 11/1998 | Duane et al. |
| 5,843,028 A | 12/1998 | Weaver et al. |
| 5,849,016 A | 12/1998 | Suhr |
| 5,851,189 A | 12/1998 | Forber |
| 5,891,056 A | 4/1999 | Ramzipoor |
| 5,919,004 A | 7/1999 | Christenson |
| 5,921,971 A | 7/1999 | Agro et al. |
| 5,931,833 A | 8/1999 | Silverstein |
| 5,935,114 A | 8/1999 | Jang et al. |
| 5,978,699 A | 11/1999 | Fehse et al. |
| 6,007,522 A | 12/1999 | Agro et al. |
| 6,053,861 A | 4/2000 | Grossi |
| RE36,702 E | 5/2000 | Green et al. |
| 6,096,009 A | 8/2000 | Windheuser et al. |
| 6,106,487 A | 8/2000 | Duane et al. |
| 6,152,910 A | 11/2000 | Agro et al. |
| 6,190,333 B1 | 2/2001 | Valencia |
| 6,190,358 B1 | 2/2001 | Fitzmaurice et al. |
| 6,200,262 B1 | 3/2001 | Ouchi |
| 6,245,437 B1 | 6/2001 | Shiiki et al. |
| 6,254,529 B1 * | 7/2001 | Ouchi ............... 600/154 |
| 6,277,100 B1 | 8/2001 | Raulerson et al. |
| 6,312,404 B1 | 11/2001 | Agro et al. |
| 6,322,577 B1 | 11/2001 | McInnes |
| 6,346,093 B1 | 2/2002 | Allman et al. |
| 6,517,518 B2 | 2/2003 | Nash et al. |
| 6,520,951 B1 | 2/2003 | Carrillo, Jr. et al. |
| 6,582,401 B1 | 6/2003 | Windheuser et al. |
| 6,606,515 B1 | 8/2003 | Windheuser et al. |
| 6,607,529 B1 | 8/2003 | Jones et al. |
| 6,663,597 B1 | 12/2003 | Windheuser et al. |
| 6,663,598 B1 | 12/2003 | Carrillo, Jr. et al. |
| 6,679,872 B2 | 1/2004 | Turovskiy et al. |
| 6,746,442 B2 | 6/2004 | Agro et al. |
| 6,746,466 B2 | 6/2004 | Eidenschink et al. |
| 6,764,484 B2 | 7/2004 | Richardson et al. |
| D498,992 S | 11/2004 | Bloom |
| 6,827,683 B2 | 12/2004 | Otawara |
| 6,827,718 B2 | 12/2004 | Hutchins et al. |
| 6,851,424 B2 | 2/2005 | Scopton |
| 6,863,661 B2 | 3/2005 | Carrillo, Jr. et al. |
| 6,869,416 B2 | 3/2005 | Windheuser et al. |
| 6,879,854 B2 | 4/2005 | Windheuser et al. |
| 6,893,393 B2 | 5/2005 | Carrillo |
| 6,925,323 B2 | 8/2005 | Snoke |
| 6,997,908 B2 | 2/2006 | Carrillo, Jr. et al. |
| 7,009,837 B2 | 3/2006 | Lo |
| 7,037,293 B2 | 5/2006 | Carrillo et al. |
| 7,060,052 B2 | 6/2006 | Windheuser et al. |
| 7,076,285 B2 | 7/2006 | Windheuser et al. |
| 7,160,283 B2 | 1/2007 | Richardson et al. |
| 7,172,577 B2 | 2/2007 | Mangano et al. |
| 7,178,520 B2 | 2/2007 | Scopton |
| 7,179,252 B2 | 2/2007 | Agro et al. |
| 2001/0029362 A1 | 10/2001 | Sirhan et al. |
| 2002/0007152 A1 | 1/2002 | Hermann et al. |
| 2002/0016612 A1 | 2/2002 | Ashby et al. |
| 2003/0088153 A1 | 5/2003 | Carrillo, Jr. et al. |
| 2003/0208104 A1 * | 11/2003 | Carrillo et al. ............... 600/159 |
| 2003/0233043 A1 | 12/2003 | Windheuser et al. |
| 2004/0106852 A1 | 6/2004 | Windheuser et al. |
| 2004/0162465 A1 * | 8/2004 | Carrillo ............... 600/104 |
| 2004/0193142 A1 | 9/2004 | Agro et al. |
| 2005/0059890 A1 | 3/2005 | Deal et al. |
| 2005/0090835 A1 | 4/2005 | Deal et al. |
| 2005/0148820 A1 | 7/2005 | Carrillo |
| 2005/0165277 A1 | 7/2005 | Carrillo, Jr. et al. |
| 2005/0203543 A1 * | 9/2005 | Hilal et al. ............... 606/108 |
| 2006/0135978 A1 * | 6/2006 | Franer ............... 606/185 |
| 2006/0142734 A1 | 6/2006 | Carrillo, Jr. et al. |
| 2006/0195117 A1 * | 8/2006 | Rucker et al. ............... 606/108 |
| 2006/0229496 A1 | 10/2006 | Windheuser et al. |
| 2007/0238928 A1 * | 10/2007 | Maseda et al. ............... 600/153 |
| 2007/0244356 A1 | 10/2007 | Carrillo, Jr. et al. |
| 2007/0293719 A1 | 12/2007 | Scopton et al. |
| 2008/0194913 A1 | 8/2008 | Tinkham et al. |
| 2008/0249362 A1 * | 10/2008 | Jiang et al. ............... 600/121 |

FOREIGN PATENT DOCUMENTS

| | | |
|---|---|---|
| DE | 199 16 866 A1 | 10/1999 |
| EP | 0 328 760 A2 | 8/1989 |
| EP | 0 388 112 A2 | 9/1990 |
| EP | 0 792 657 A2 | 9/1997 |
| EP | 0 801 955 B1 | 10/1997 |
| EP | 1 779 764 A1 | 5/2007 |
| JP | 50-108287 U | 9/1975 |
| JP | 3-126428 A | 5/1991 |
| JP | 6-23055 A | 2/1994 |
| JP | 7-155382 A | 6/1995 |
| JP | 9-94253 A | 4/1997 |
| WO | WO 92/03963 A1 | 3/1992 |
| WO | WO 96/13296 A1 | 5/1996 |
| WO | WO 96/33764 A1 | 10/1996 |
| WO | WO 98/10820 A1 | 3/1998 |
| WO | WO 98/10821 A1 | 3/1998 |
| WO | WO 99/38557 A1 | 8/1999 |
| WO | WO 99/59664 A1 | 11/1999 |
| WO | WO 00/69499 A1 | 11/2000 |
| WO | WO 00/69500 A1 | 11/2000 |

OTHER PUBLICATIONS

Knecht, Gregory L., M.D. et al., "Double-Channel Fistulotome for Endoscopic Drainage of Pancreatic Pseudocyst," *Gastrointestinal Endoscopy*, vol. 37, No. 3, May/Jun. 1991, pp. 356-357.

Siegel, Jerome H., M.D. et al., "Two New Methods for Selective Bile Duct Cannulation and Sphincterotomy," *Gastrointestinal Endoscopy*, vol. 33, No. 6, Dec. 1987, pp. 438-440.

* cited by examiner

INTEGRATED LOCKING DEVICE WITH ACTIVE SEALING

CROSS-REFERENCE TO RELATED APPLICATIONS

This application claims the benefit of U.S. Provisional Application No. 61/054,393, filed May 19, 2008, the entire disclosure of which is incorporated herein by reference.

This application is related to U.S. patent application Ser. No. 12/467,962, filed on May 18, 2009 and entitled "Integrated Locking Device with Passive Sealing", which claims the benefit of U.S. Provisional Application Ser. No. 61/054,407, filed May 19, 2008; U.S. patent application Ser. No. 12/467,968, entitled "Integrated Locking Device with Fluid Control", filed on May 18, 2009, which claims the benefit of U.S. Provisional Application No. 61/054,413, filed May 19, 2008; and U.S. patent application Ser. No. 12/467,947, filed on May 18, 2009 and entitled "Biopsy Cap Attachment and Integrated Locking Device", which claims the benefit of U.S. Provisional Application Ser. No. 61/054,294, filed May 19, 2008, which disclosures are all hereby incorporated herein by reference. This application is also related to U.S. patent application Ser. No. 12/029,148, filed Feb. 11, 2008, the disclosure of which is here by incorporated herein by reference.

FIELD OF THE INVENTION

The present invention pertains to endoscopes, endoscope assemblies, guidetubes, introducers, and instrument caps for endoscopes, guidetubes, and introducers. More particularly, the present invention pertains to biopsy caps for an access port of an endoscope.

BACKGROUND

A wide variety of endoscope assemblies and biopsy caps have been developed. Of the known endoscope assemblies and biopsy caps, each has certain advantages and disadvantages. There is an ongoing need to provide alternative endoscope assemblies and biopsy caps as well as methods for making and using the same.

BRIEF SUMMARY

The invention provides design, material, and manufacturing method alternatives for endoscope assemblies and biopsy caps as well as provides methods for making and using endoscope assemblies and biopsy caps.

An example endoscope assembly may include an endoscope having a channel formed therein and a port that provides access to the channel. A cap may be coupled to the port. The cap may include a base and an outer shell. A locking member may be coupled to the shell. An inner seal member may be disposed within the shell. One or more openings may extend through the cap and into the channel. An actuator may be coupled to the base for shifting the inner seal member between an unsealed configuration and a sealed configuration.

An example endoscope biopsy cap may include an outer shell having an opening formed therein and a base. A locking member may be coupled to the shell for securing the position of a medical device disposed in the opening. An inner seal member may be disposed within the shell. An actuator may be coupled to the base for shifting the inner seal member between an unsealed configuration and a sealed configuration.

Another example biopsy cap may include a base portion for attaching the biopsy cap to an endoscope. The biopsy cap may also include a body portion. A compression seal member may be disposed within the body portion. The compression seal member may be configured to shift between a sealed configuration and an unsealed configuration. A collet may be coupled to the body portion.

Another example endoscope biopsy cap may include an outer shell and a seal disposed within the shell. The seal may include a helically-oriented sealing gasket.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
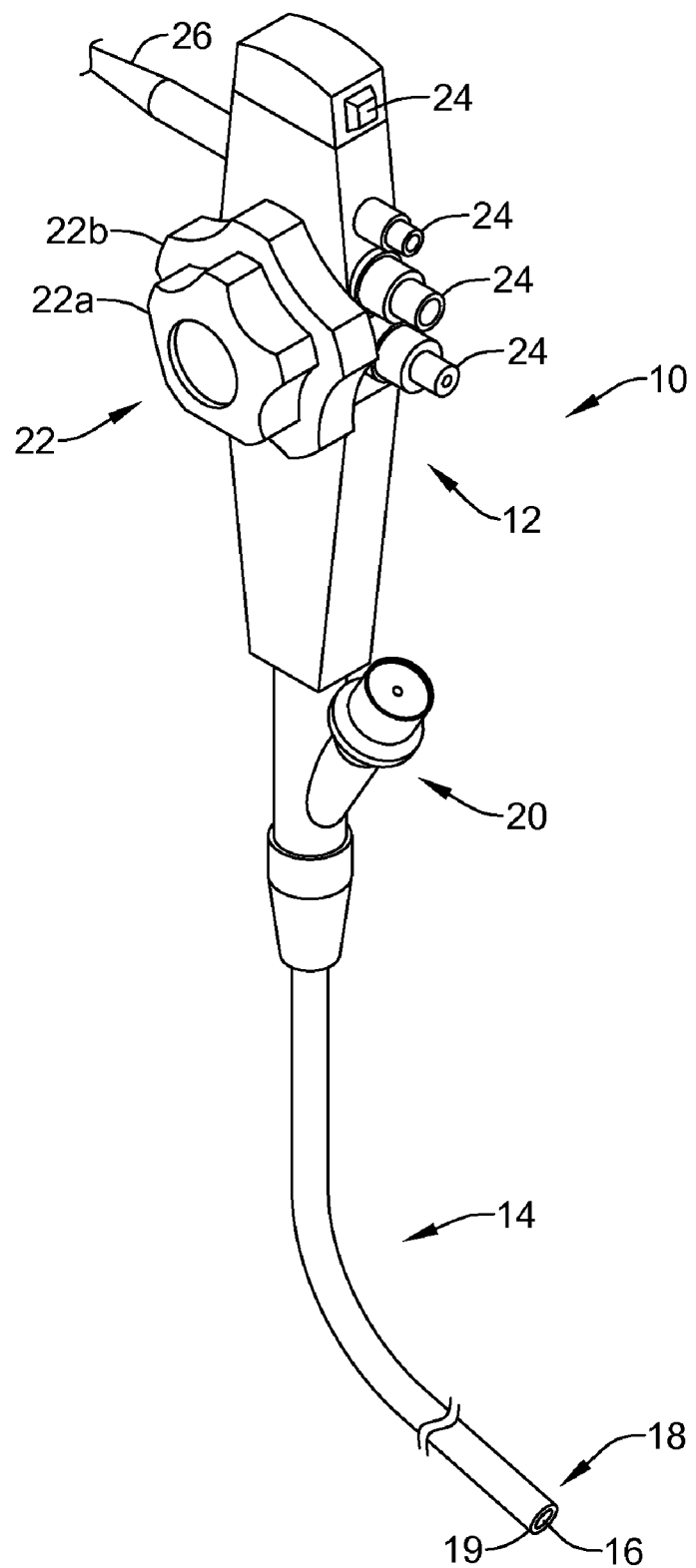
FIG. 1 is a perspective view of an example endoscope assembly.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

An example endoscope and/or endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guidetubes, introducers (without or without vision or visualization capabilities), or any other type of endoscope or related medical device. Endoscope 10 may include a handpiece 12 and an elongate shaft 14 extending distally from handpiece 12 to a distal tip 18. Shaft 14 may include a lumen defining a working channel 16 extending through shaft 14 from a distal end 19 near distal tip 18 of shaft 14 to an access port 20 that may be positioned in handpiece 12 or another portion of endoscope 10. Although endoscope 10 is depicted with a single working channel in FIG. 1, it can be appreciated that in other embodiments, endoscope 10 may include multiple working channels, as desired.

Handpiece 12 may include one or a plurality of controls 22, such as rotating knobs, which may be used to control movement of distal tip 18 of shaft 14 during operation. For example, a first rotating knob 22a may control up and down movement or deflection of distal tip 18 of shaft 14, while a second rotating knob 22b may control side-to-side movement or deflection of distal tip 18 of shaft 14. Handpiece 12 may also include one or a plurality of buttons 24, which may be used to activate suction or deliver fluid such as air, saline and/or water, etc. through a lumen of the endoscope 10 or perform other functions as desired. Additionally, handpiece 12 may include an optical cable 26 connected to an external light source (not shown).

Figure 2:
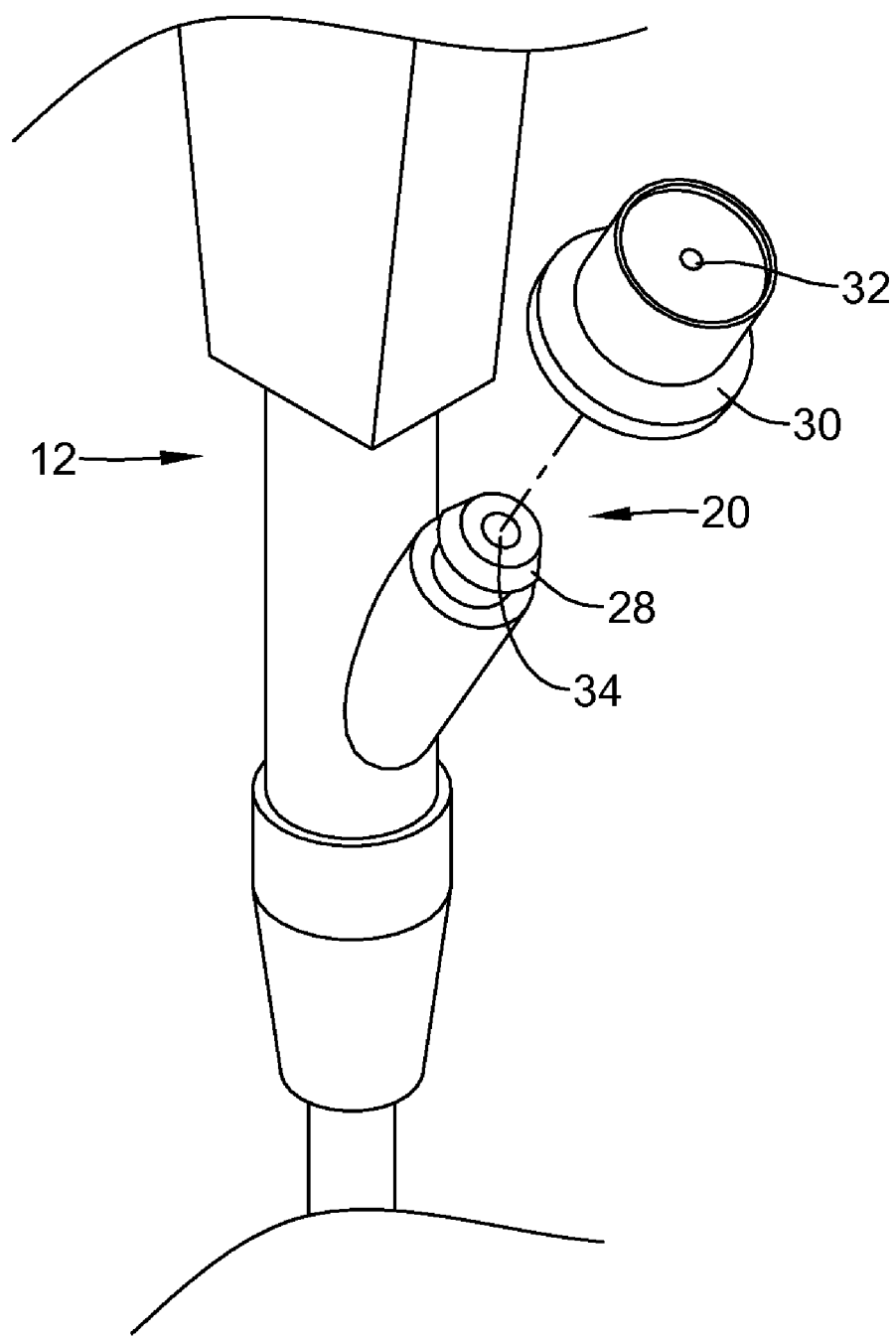
FIG. 2 is an exploded view of a portion of the example endoscope assembly shown in FIG. 1 illustrating a biopsy cap.

Turning now to FIG. 2, here access port 20 of handpiece 12, which provides access to working channel 16 of endoscope 10, is illustrated. Access port 20, which may extend from the side of endoscope 10 or at another location, may include a coupling portion 28 for coupling a cap 30 to access port 20. Cap 30, which may be removably attached or permanently attached to access port 20, may provide access for inserting and/or advancing an endoscopic device through working channel 16 of endoscope 10.

Caps like cap 30, which may be termed "biopsy caps", are often designed with several functions in mind. For example, cap 30 may form a fluid/air barrier to working channel 16 that may help control insufflation and bile fluid egress therefrom that later have the potential to spill onto the clinician's hands and/or the floor thereby interfering with the intervention and/or become a biohazard. In addition, cap 30 may have an opening 32 extending therethrough. Opening 32 may be in fluid communication with working channel 16 and it may reduce the size of the opening 34 of working channel 16, for example, to accommodate an endoscopic device or instrument. Thus, caps like cap 30 may be much like an adapter in that it forms a physical transition at opening 34 of working channel 16 so that it transitions to a size more closely to that of the device to be inserted into working channel 16. Some additional discussion regarding biopsy caps can be found in U.S. Patent Application Pub. Nos. US2007/0293719A1, US2007/0244356A1, and US2007/0238928A1, the entire disclosures of which are herein incorporated by reference.

A number of additional biopsy caps are contemplated that incorporate at least some of the desirable features of biopsy caps as well as have other desirable characteristics. The forgoing discussion discloses some of the embodiments of caps that are contemplated. These caps may include an active seal.

For the purposes of this disclosure, an active seal is a seal that seals endoscope 10 at port 20 so as to prevent the leakage of bodily fluids and/or air when actuated by a user. In addition, by virtue of being "active", the caps disclosed herein are configured to be selectively activated so as to seal off endoscope 10 at port 20 at any appropriate time during an intervention and, conversely, may also be configured to be "unlocked" or "unsealed" at the desired time by a clinician.

Figure 3:
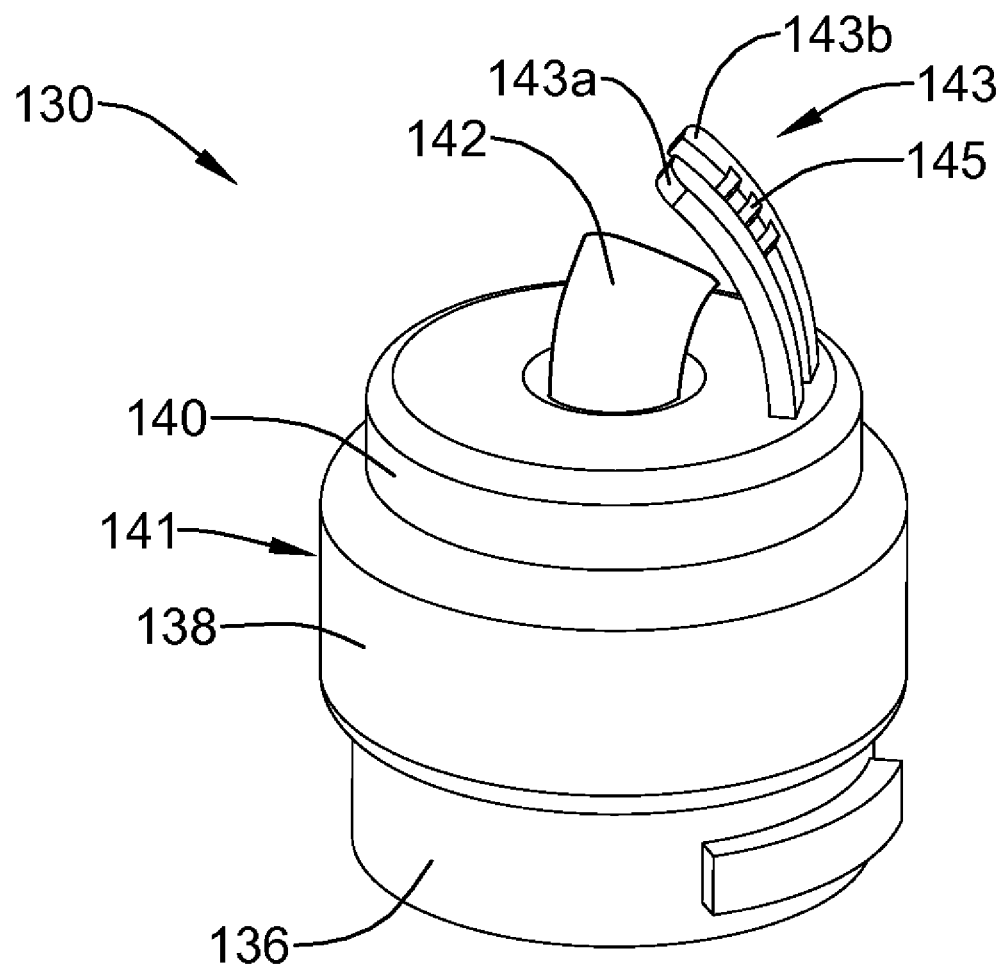
FIG. 3 is a perspective view of an example biopsy cap.
Figure 4:
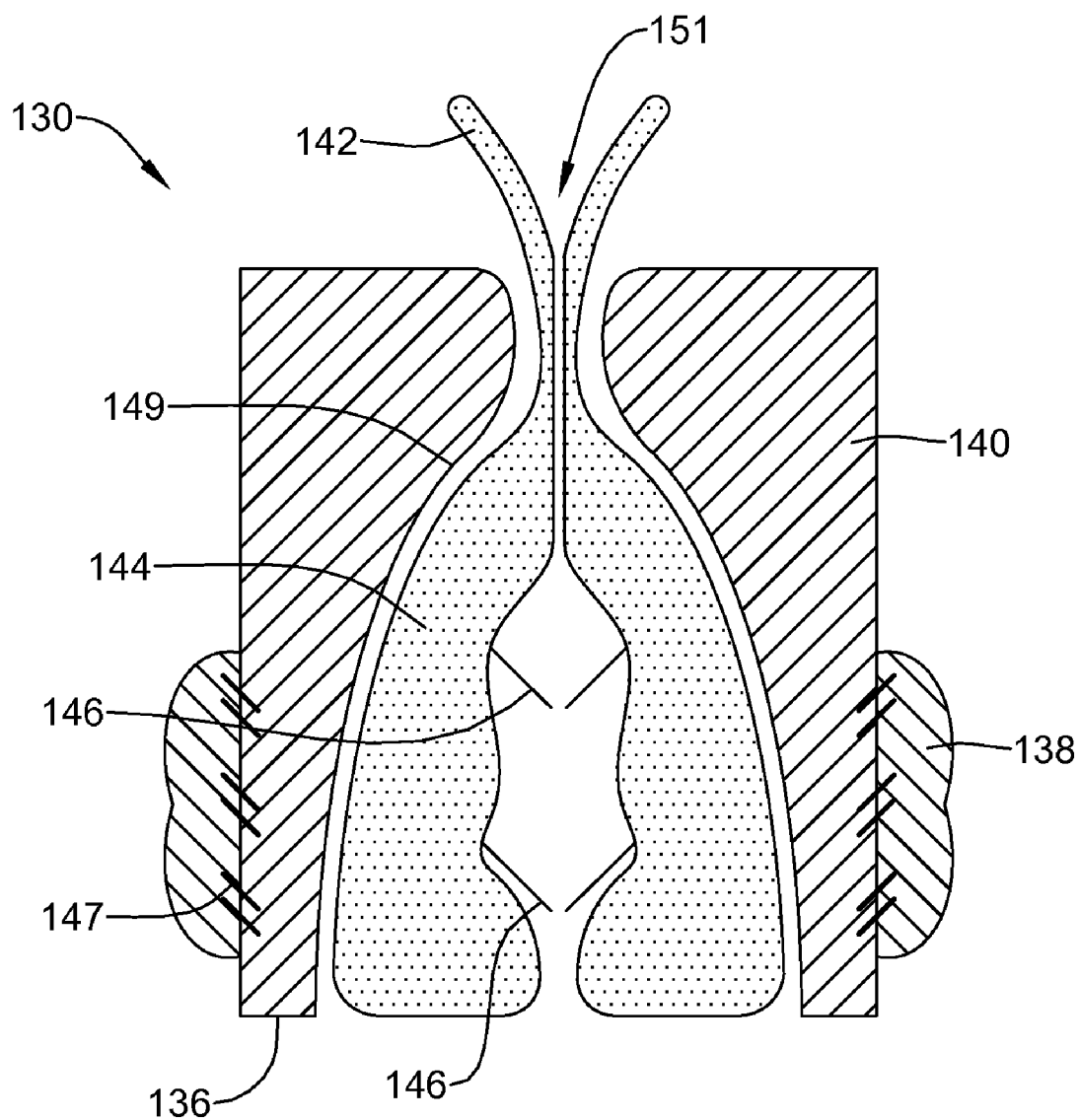
FIG. 4 is a partial cross-sectional view of the example biopsy cap illustrated in FIG. 3.

Turning now to the remaining figures, FIG. 3 is a perspective view of biopsy cap 130, which may be similar in form and function to other caps disclosed herein. FIG. 4 is a partial cross-sectional view of cap 130. Cap 130 may include a base portion 136, an actuator ring 138, a chuck 140, a strain relief 142, and one or more locking members 143. Base 136, ring 138 and chuck 140 may, collectively, define or otherwise be disposed along an outer shell or covering 141 of cap 130. Within shell 141, cap 130 may include an inner seal member 144, as illustrated in FIG. 4. Shell 141 may take a number of different shapes and forms. In general, however, shell 141 is made from or otherwise includes a relatively rigid or hard polymer/plastic, a metal or metal alloy, a ceramic, and the like, or combinations thereof and may take a form resembling an exoskeleton or protective covering over the more delicate interior (e.g., seal member 144). In addition, by virtue of forming shell 141 from a relatively rigid material, a number of accessories to and/or structural components of cap 130 may be secured to or integrally formed with shell 141. For example, locking member(s) 143 may be secured to or integrally formed with shell 141.

The various portions of shell 141 may include a number of desirable structural characteristics and/or features that may impact cap 130. For example, base 136 may be disposed on a bottom surface of cap 130 and may include one or more structures for attaching cap 130 to port 20 including, for example, a securing member. The form or configuration of the securing member may vary considerably. For example, base 136 may include a pair or set of locking tabs that are configured to "snap" onto port 20. Numerous alternative securing members are contemplated for cap 130 and other caps disclosed herein. Examples of some of the various alternative securing members contemplated can be found below.

Figure 4A:
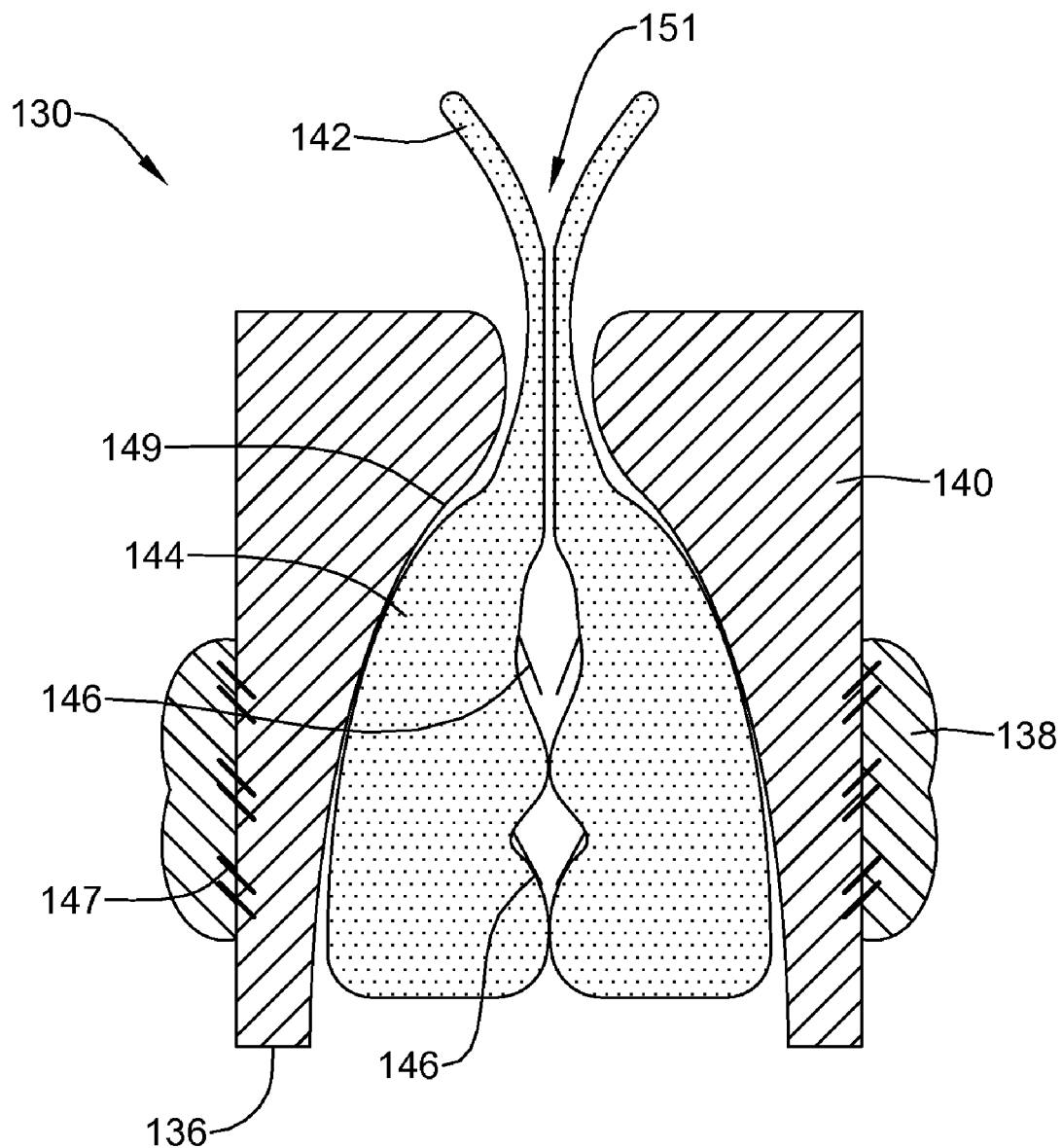
FIG. 4A is a partial cross-sectional view of the example biopsy cap illustrated in FIG. 4 in another configuration.
Figure 4B:
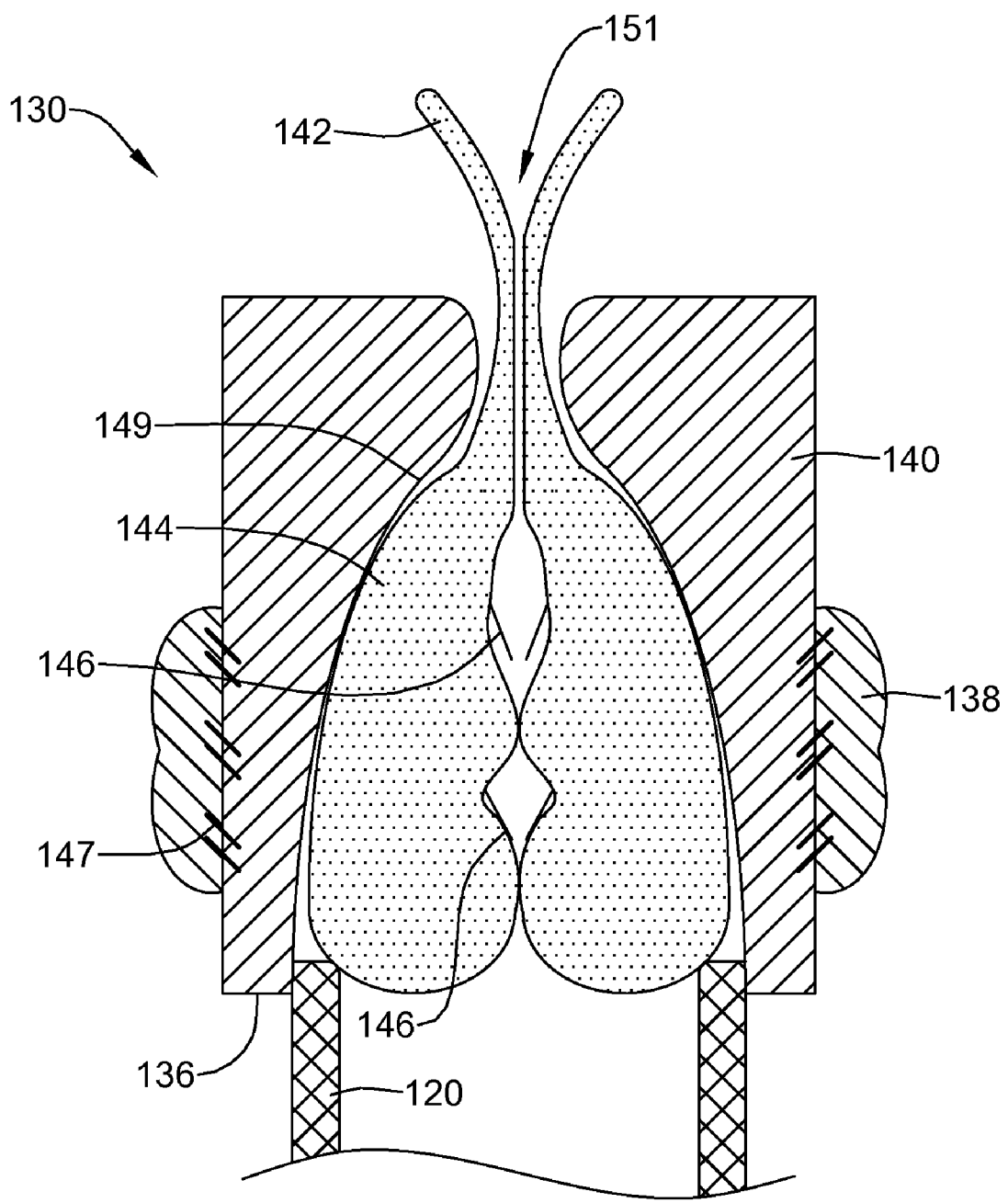
FIG. 4B is a partial cross-sectional view of the example biopsy cap illustrated in FIG. 4 and FIG. 4A attached to an endoscope port.

Ring 138 and chuck 140 may be disposed above base 136. In at least some embodiments, ring 138 may be rotatably arranged with respect to chuck 140. For example, rotating ring 138 may cause chuck 140 to move and, therefore, apply a force onto seal member 144. The relative movement between chuck 140 and ring 138 may be accomplished in a number of different ways. For example, a series of threads 147 may be formed on chuck 140 and ring 138 so that rotating ring 138 causes chuck 140 to be urged downward. Doing so may cause a shoulder region 149 of chuck 140 to press against and deform seal member 144 as illustrated in FIG. 4A. This may cause seal member 144 to seal against a device extending therethrough, to seal cap 130 against port 20, or both. Thus, ring 138 may be used to shift seal member 144 between a sealed configuration and an unsealed configuration. With this amount or a further amount of rotation, seal member 144 may be deformed such that cap 130 may be fitted over a port 120 of an endoscope and secured thereto, for example, with a butt seal or joint as illustrated in FIG. 4B.

In some alternative embodiments, seal member 144 may be shifted in another manner. For example, shell 141 may include a ratchet member that can be ratcheted to shift seal member 144. Alternatively, a depressible button actuator can be used to shift seal member 144. According to this embodiment, pressing the button may cause shell 141 and/or seal member 144 to shift. In still other embodiments, shell 141 may be deformable so that it can be simply squeezed or otherwise deformed to shift seal member 144.

Seal member 144 may comprise a soft material such as a plastic or foam that may be suitable for sealing about a medical device extending therethrough. The precise form and materials for seal member 144 may vary. For example, seal member 144 may include a pliable or formable material that may or may not be absorbent. In some embodiments, seal member 144 may include those materials used for similar structures disclosed in U.S. Pat. No. 6,663,598, the entire disclosure of which is herein incorporated by reference. In at least some embodiments, seal member 144 may substantially fill the interior of shell 141. Alternatively, portions of the interior of shell 141 may lack seal member 144 and may be used, for example, to hold bodily fluids that may escape from port 20.

Seal member 144 may also include one or more flaps or membranes 146. Flaps 146 may be arranged, for example, in a series of horizontal layers that are stacked vertically. Each layer may include one or more flaps 146 that may or may not overlap with one another. Numerous other arrangements are also contemplated. By arranging flaps 146 in the manner illustrated in FIG. 4, each layer or set of flaps 146 may form a "seal" such that flaps 146 may define a plurality of seals. If one of these seals (e.g., the layer of flaps 146 closest to base 136) should be compromised, an adjacent seal would maintain the integrity of seal member 144, and so on. Thus, the multi-layer design of seal member 144 may enhance the ability of cap 130 to prevent the leakage of bodily fluids during a medical intervention.

The number of flaps 146 utilized in seal member 144 as well as the number of layers may vary. For example, each layer may include one, two, three, four, five, six, seven, eight, or more flaps 146. Likewise, seal member 144 may include one, two, three, four, five, six, seven, eight, or more layers of flaps 146. In some embodiments, each layer may include the same number of flaps 146. In other embodiments, differing numbers of flaps 146 may be used in different layers.

One or more apertures 151 may be formed in cap 130 that may be the entrance point or otherwise define one or more openings that extend through cap 130 into channel 16 when cap 130 is seated on port 20. Thus, aperture 151 may form the exterior opening in cap 130 where other medical devices (e.g., guidewires, catheters, etc.) can be passed through so as to gain access to working channel 16.

Strain relief 142 may be disposed adjacent aperture 151, for example, with aperture 151 extending through strain relief 142. In general, strain relief 142 may be positioned a distance away from port 20 so that strain relief 142 may relieve strain that might otherwise be applied to endoscope 10 (e.g., at port 20), for example, during device exchanges or transfers. Thus, the shear stress that may be generated during device exchanges can be shifted away from endoscope 10, which may improve the ability of cap 130 to maintain a good seal at port 20.

Strain relief 142 may be formed of a relatively flexible material that can be bent or deformed relatively easily and without transferring other forces to other portions of cap 130. Accordingly, strain relief 142 may be bent or deformed, for example, when a device (e.g., guidewire, catheter, etc.) that is extending therethrough is moved or shifted within channel 16. In addition, should the device need to be exchanged, strain relief 142 may be able to absorb the shear stresses associated with such a manipulation. In some embodiments, strain relief 142 may be a distinct structure that is disposed along the top surface of cap 130. In other embodiments, strain relief 142 may be a portion of seal member 144 that, for example, extends out from the top of cap 130.

Locking members 143 may be generally disposed adjacent the top surface of cap 130 and they may be used to secure and/or hold the position of a device (e.g., a guidewire, catheter, etc.) extending through cap 130 into channel 16. For example, locking members 143 may include one or more bends or "hooks" formed therein that a medical device may be wrapped around or pressed against to hold its position. The number of locking members 143 may vary. In some embodiments, one locking member 143 is utilized. In other embodiments, two, three, four, five, six, or more locking members 143 are utilized.

In cap 130, locking member 143 is shown with two locking members 143a/143b. Member 143a may take the form of a rod or shaft. Member 143b may similarly resemble a rod but it may also include one or more grooves or slots 145. Locking member 143 may function in a number of different ways. For example, locking member 143 may secure the position of a device by disposing the device between members 143a/143b, in slots 145, around one or both of members 143a/143b, etc. While this form of locking member 143 is illustrated in FIG. 3, it can be appreciated that the precise form of locking member 143 may vary. Examples of some of the various alternative locking members 143 contemplated can be found below.

Figure 5A:
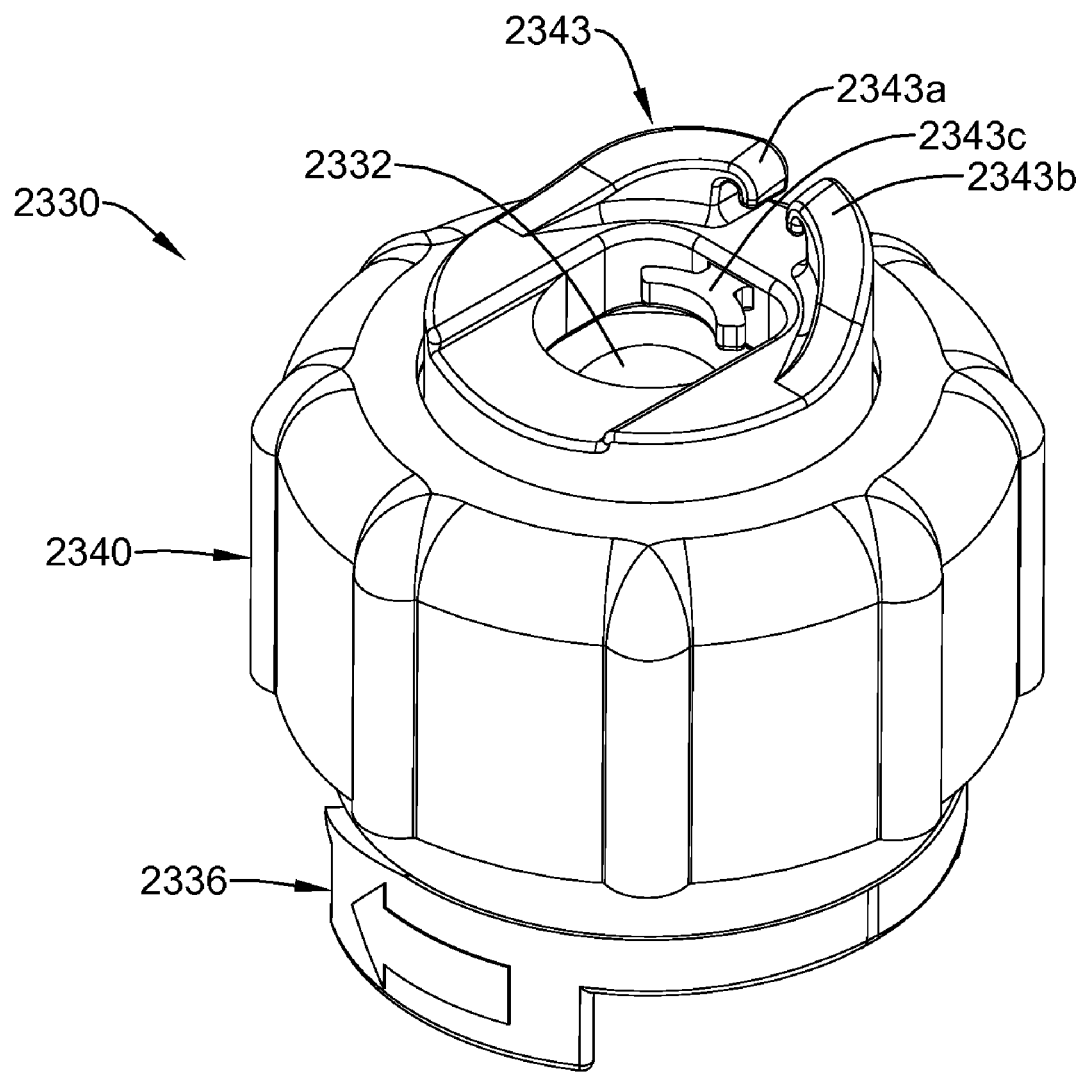
FIG. 5A is a perspective view of another example biopsy cap.

FIG. 5A illustrates another example cap 2330 that may be similar in form and function to other caps disclosed herein. Cap 2330 may include a base 2336, a body portion 2340, a locking portion 2343, and a opening 2332. Locking portion 2343 may include a plurality of locking members including locking members 2343a/2343b/2343c. Locking members 2343a/2343b/2343c may be similar in form and function to any of locking members or similar structures disclosed herein. For example, any of locking members 2343a/2343b/2343c may include one or more hooks or securing portions for securing a device (e.g., a guidewire, catheter, etc.) disposed in opening 2332. Opening 2332 may provide access to channel 16 when cap 2330 is attached to endoscope 10.

Figure 5B:
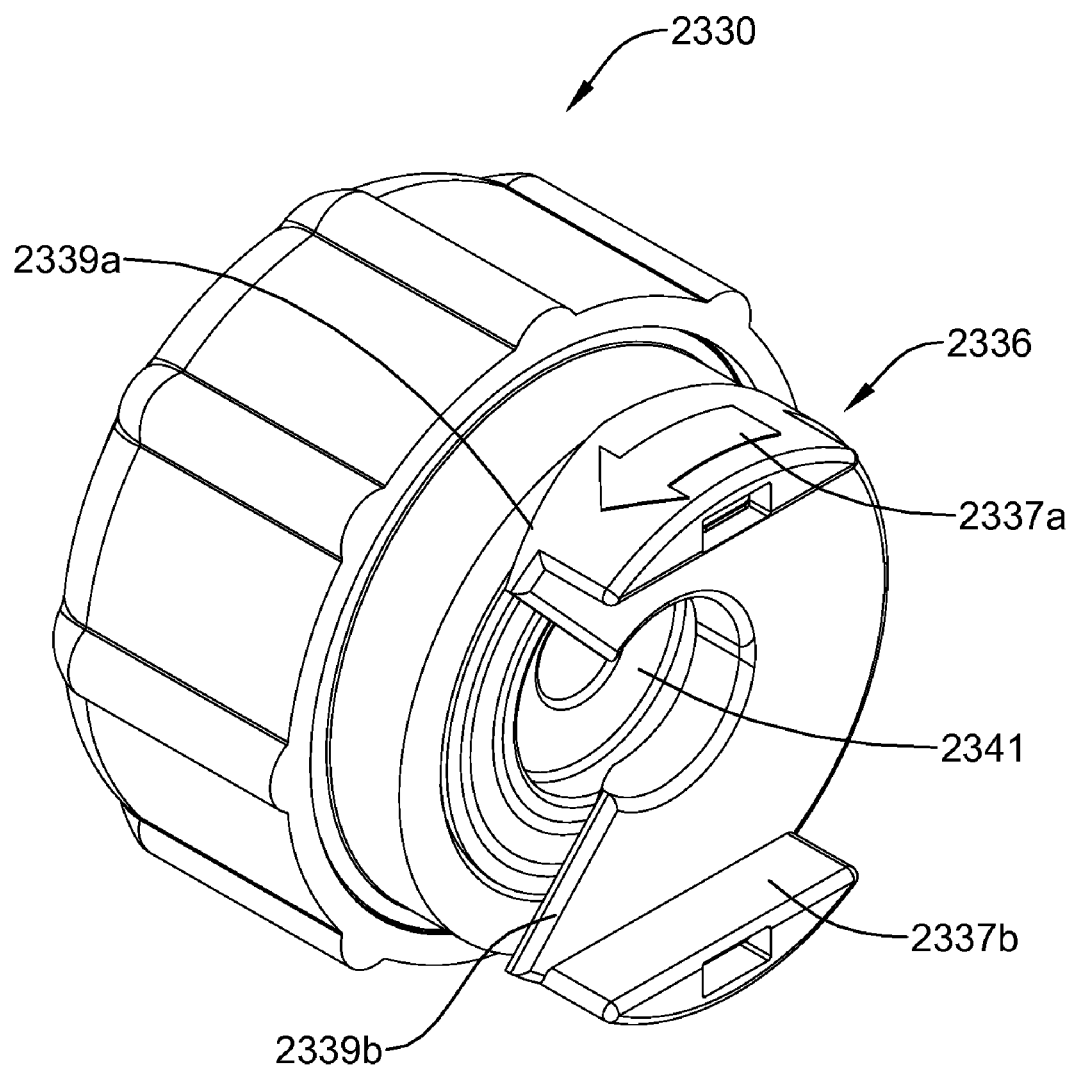
FIG. 5B is a bottom view of the biopsy cap illustrated in FIG. 5A.

FIG. 5B is a bottom view of cap 2330 showing base 2336. Here it can be seen that base 2336 may include a pair of clips 2337a/2337b. Clips 2337a/2337b may be spaced apart and have an opening between that can accommodate port 20 and allow cap 2330 to be securely attached to endoscope 10. Base 2336 may include ramped surfaces 2339a/2339b that are disposed adjacent clips 2337a/2337b. Connecting cap 2330 to port 20 may include the user grasping clips 2337a/2337b and advancing cap 2330 over port 20 so that port 20 passes into the opening between clips 2337a/2337b, follows along ramped surfaces 2339a/2339b, and "snaps" securely onto base 2336. A gasket or seal 2341 may be disposed within cap 2330 at base 2336 that can seal against port 20 and effect a fluid tight seal between cap 2330 and port 20.

Figure 5C:
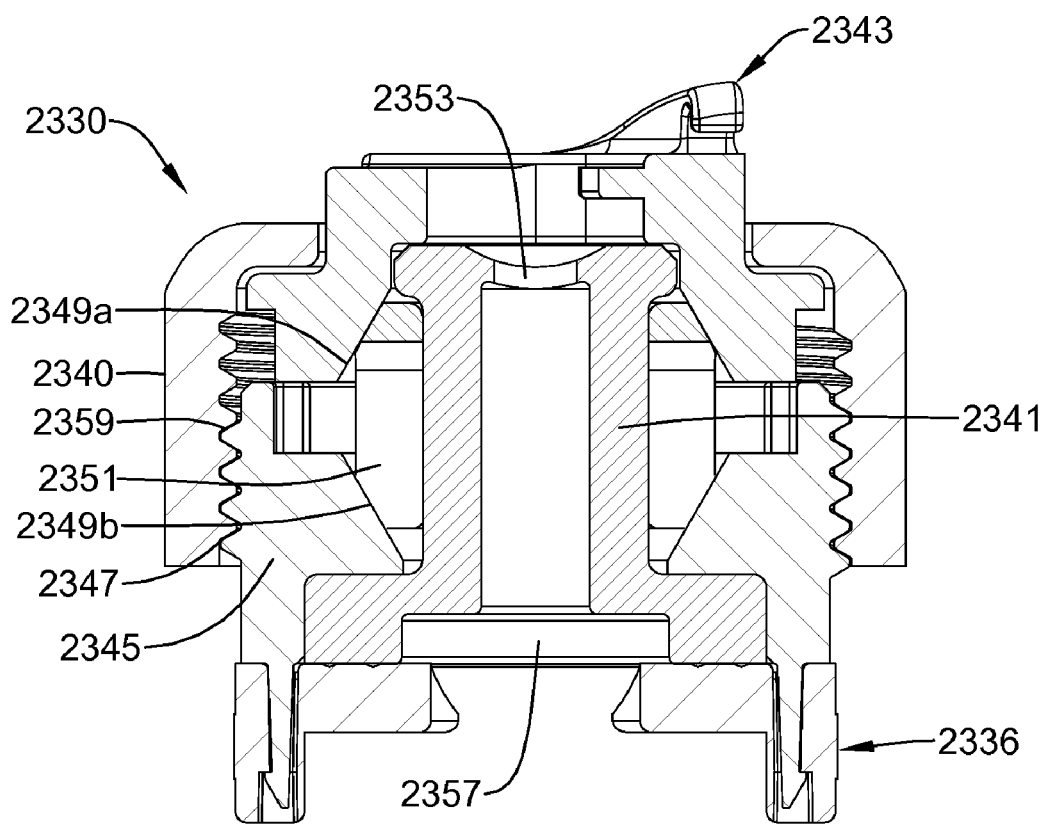
FIG. 5C is a partial cross-sectional view of the biopsy cap illustrated in FIG. 5A.

FIG. 5C is a partial cross-sectional view of cap 2330. Here it can be seen that body portion 2340 may include one or more threads 2359. Disposed adjacent body portion 2340 may be a collet 2345 that may include threads 2347. Collet 2345 may include one or more sloped surfaces including, for example, sloped surfaces 2349a/2349b.

Threads 2359 on body portion 2340 may be threadably connected with (e.g., mated with) threads 2347 on collet 2345. Body portion 2340 may be rotatable about collet 2345. Collet 2345 may be moveable within cap 2330 such that as body portion 2340 is rotated, the threaded connection between threads 2359/2347 may result in collet 2345 being urged downward. As collet 2345 is urged downward, sloped surfaces 2349a/2349b of collet 2345 may press against a compression seal member 2351 disposed within cap 2330. As sloped surfaces 2349a/2349b press against compression seal member 2351, compression member 2351 deforms radially inward and effects a seal against a device (e.g., a guidewire, catheter, etc.) that may be extending through cap 2330.

Seal 2341 can also be seen in FIG. 5C. Seal 2341 may include a top opening 2351 that may be disposed adjacent opening 2332 of cap 2330. Top opening 2351 of seal 2341 may include a slit-type seal that includes a slit-like opening into the interior of seal 2341. Seal 2341 may also include a bottom portion 2357 having a corresponding bottom opening so that a device may extend through seal 2351 and into channel 16. Bottom portion 2357 may seal against port 20 when cap 2330 is attached to endoscope 10.

Figure 5D:
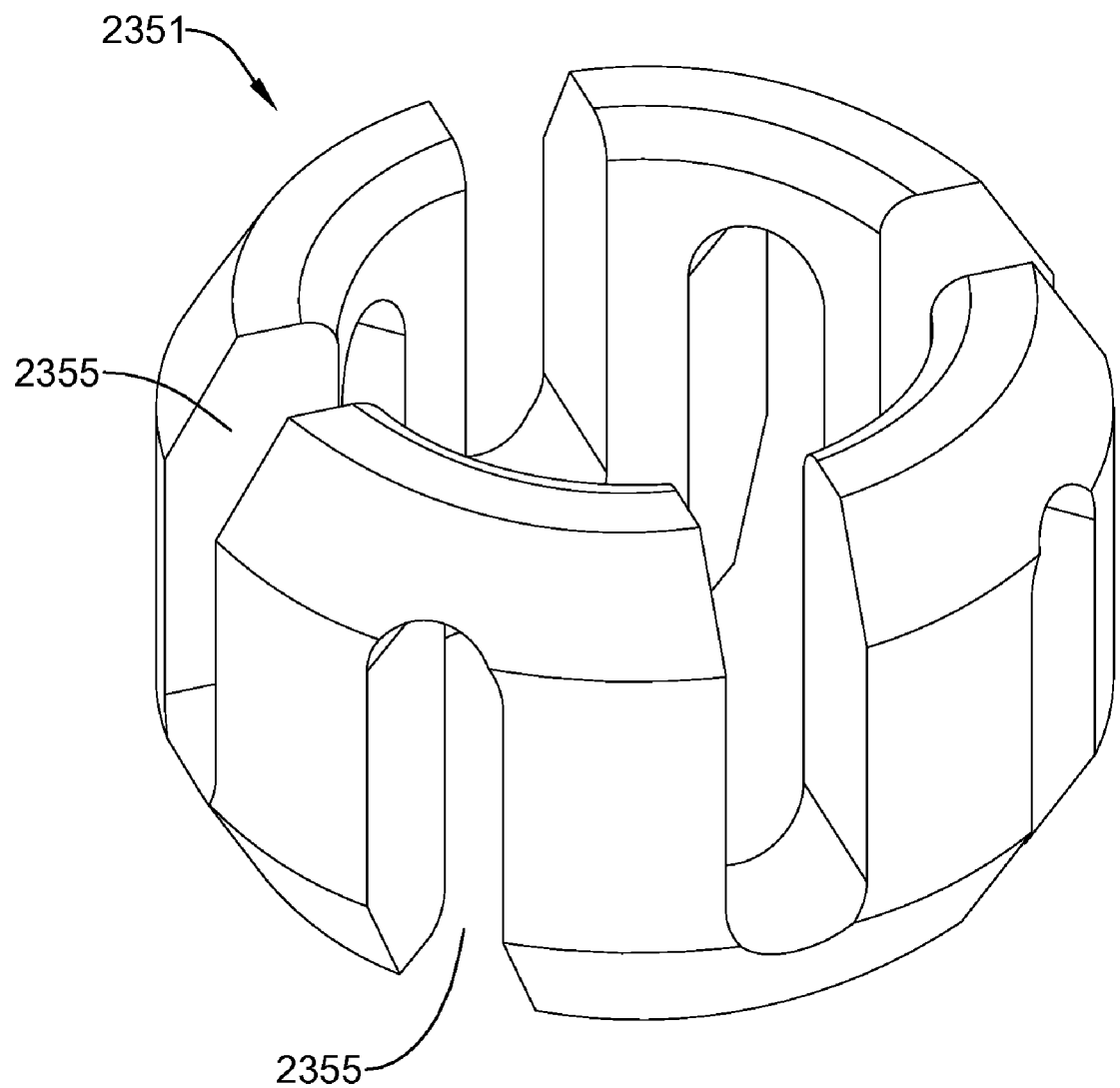
FIG. 5D is a perspective view of an example compression member for use with a biopsy cap.

FIG. 5D illustrates compression seal member 2351. Here it can be seen that compression seal member 2351 may include a plurality of gaps or cutouts 2355. In some embodiments, cutouts 2355 may be formed in the top surface of compression seal member 2351. In other embodiments, cutouts 2355 may be formed in the bottom surface of compression seal member 2351. In still other embodiments, cutouts 2355 may alternate between the top and bottom surface of compression seal member 2351, as shown.

Compression seal member 2351 may be configured to shift between a first configuration and a second configuration. In at least some embodiments, the first configuration is an uncompressed or unsealed configuration. In this configuration, compression seal member 2351 may appear as shown in FIG. 5D. The second configuration may be a compressed or sealed configuration. Shifting between configuration may occur when body portion 2340 is rotated and collet 2345 shifts in position. As indicated above, the shifting of collet 2345 causes sloped surfaces 2349a/2349b of collet 2345 to exert a force on compression seal member 2351. As sloped surfaces 2349a/2349b of collet 2345 exert a force on compression seal member 2351, compression seal member 2351 is compressed radially inward. The cutout design of compression seal member 2351 allows compression seal member 2351 to deform radially inward while cutouts 2355 allow compression seal member 2351 to deform to a smaller, more compact size.

When radially compressed, compression seal member 2351 can effect a seal around a device (e.g., a guidewire, catheter, etc.) extending through cap 2330. In some embodiments, compression seal member 2351 may directly seal against the device. In other embodiments, compression seal member 2351 indirectly seals against the device. For example, compression seal member 2351 may press against seal 2341 so that seal 2341 can directly seal against the device.

Figure 6A:
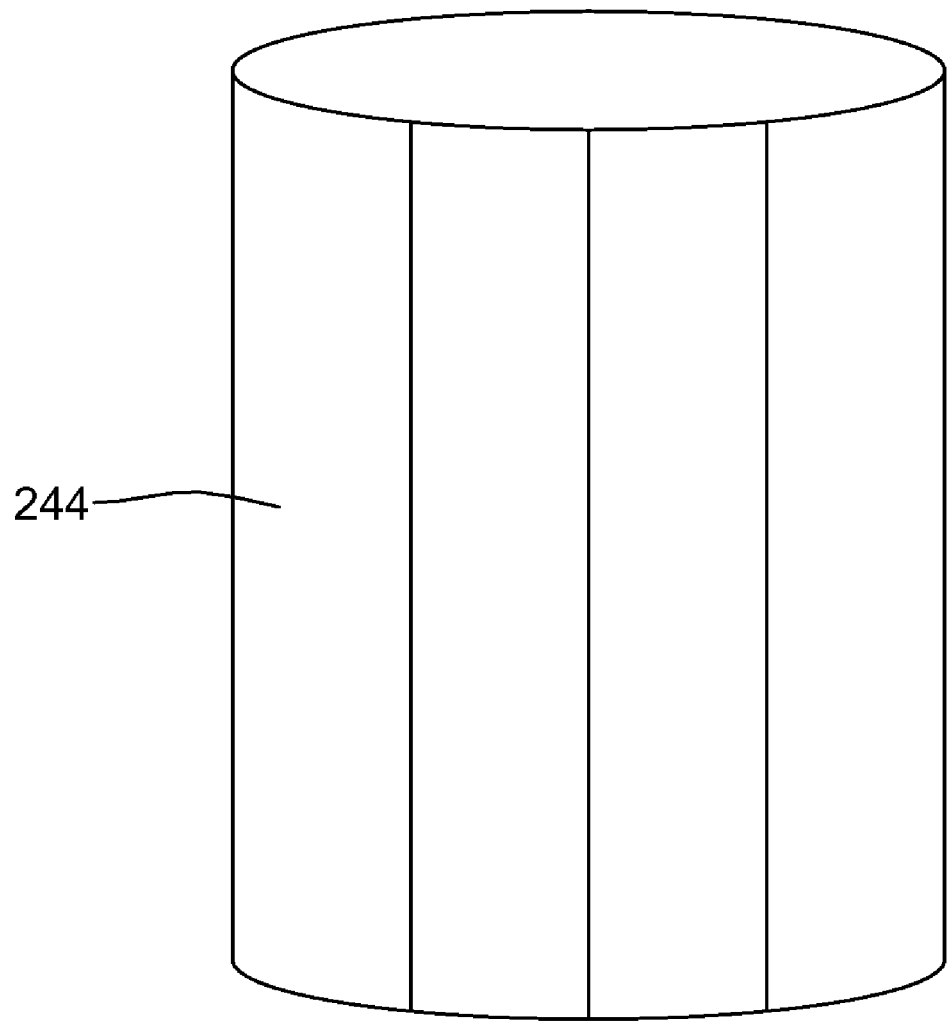
FIG. 6A is a side view of an example seal member for use with a biopsy cap.
Figure 6B:
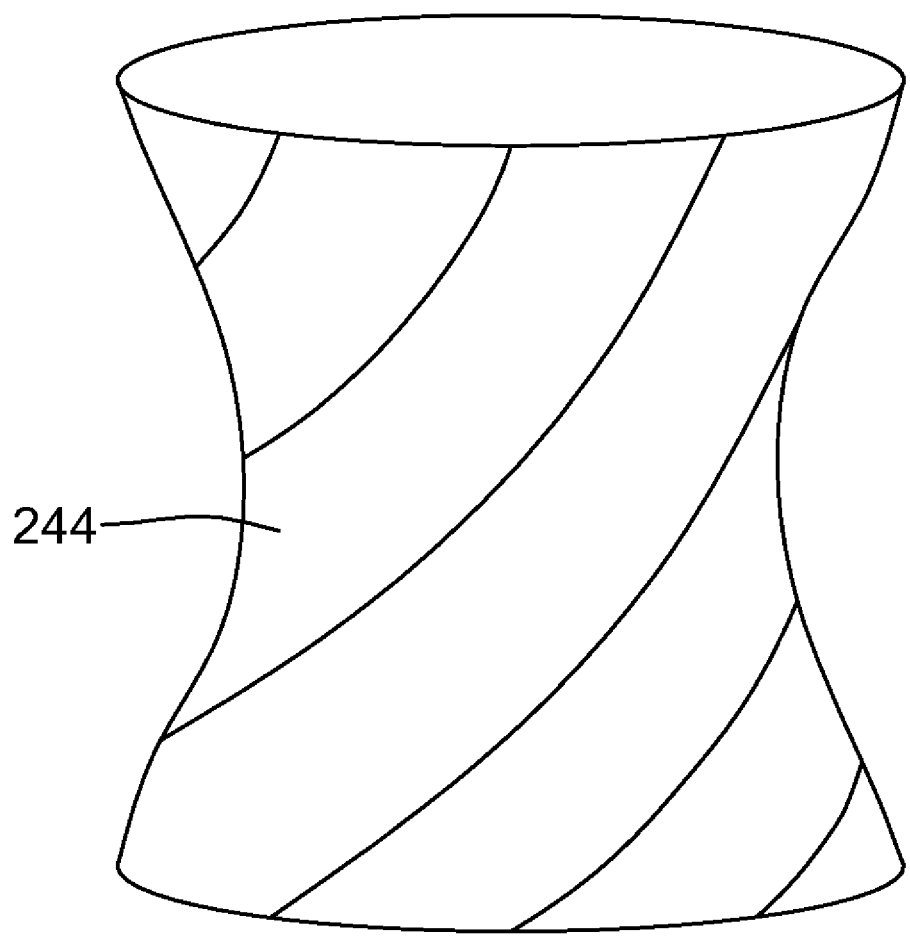
FIG. 6B is a side view of the seal member illustrated in FIG. 6A in an alternative configuration.

As indicated above with respect to FIG. 4, seal member 144 may be deformed when chuck 140 presses against it. This arrangement, however, is not intended to be limiting as other seal members are contemplated. For example, FIGS. 6A and 6B illustrate seal member 244 that may be used with any of the caps disclosed herein. Seal member 244 may be similar in form and function to other seal members except that sealing may be accomplished by twisting seal member 244. For example, seal member 244 may be coupled or attached to ring 138 so that rotation of ring 138 shifts seal member 244 from the unsealed or untwisted configuration (as illustrated in FIG. 6A) to the sealed or twisted configuration (as illustrated in FIG. 6B). When in the twisted configuration, the interior of seal member 244 may substantially press against and seal a device extending therethrough. In addition or in the alternative, seal member 244 may include an opening that extends therethrough, and when seal member 244 is twisted, the opening may shift from a larger configuration (e.g., unsealed) to a smaller configuration (e.g., sealed about the device).

Figure 7:
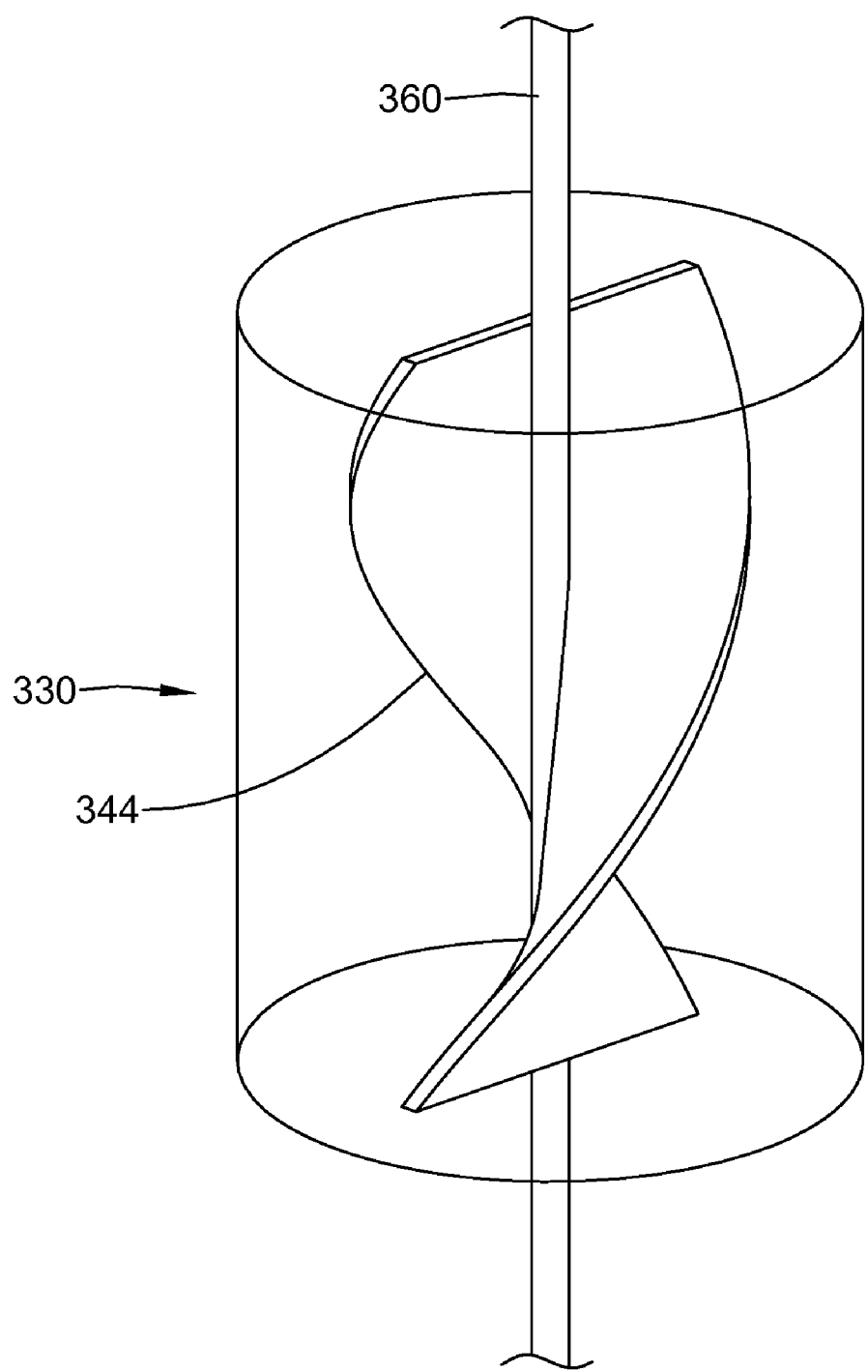
FIG. 7 is a side view of another example seal member for use with a biopsy cap.

FIG. 7 illustrates another example cap 330 that includes seal member 344, which can be used with other caps disclosed herein. Seal member 344 may take the form of a helically-oriented sealing gasket. Gasket 344 may utilize surface tension to seal against a device 360 (e.g., catheter, guidewire, etc.) extending therethrough in a manner similar, for example, to how a drop of fluid may hold together glass lab slides. Gasket 344 may be formed of a material that when wet (e.g., by bodily fluids, water, etc.) will tend to adhere to other objects like device 360. This may create a flexible dynamic seal that could conform and adjust to the various devices inserted therethrough. As indicated above, in some embodiments, gasket 344 may be helically oriented or twisted. This arrangement may create a continuous seal that is not easily disrupted by deformation or stress in any one single plane. Numerous other orientations, of course, are also contemplated. For example, the shell may be altered in another manner to cause sealing. This may include squeezing or compressing a cap in a manner sufficient to deform a seal member and seal against a device.

Figure 8:
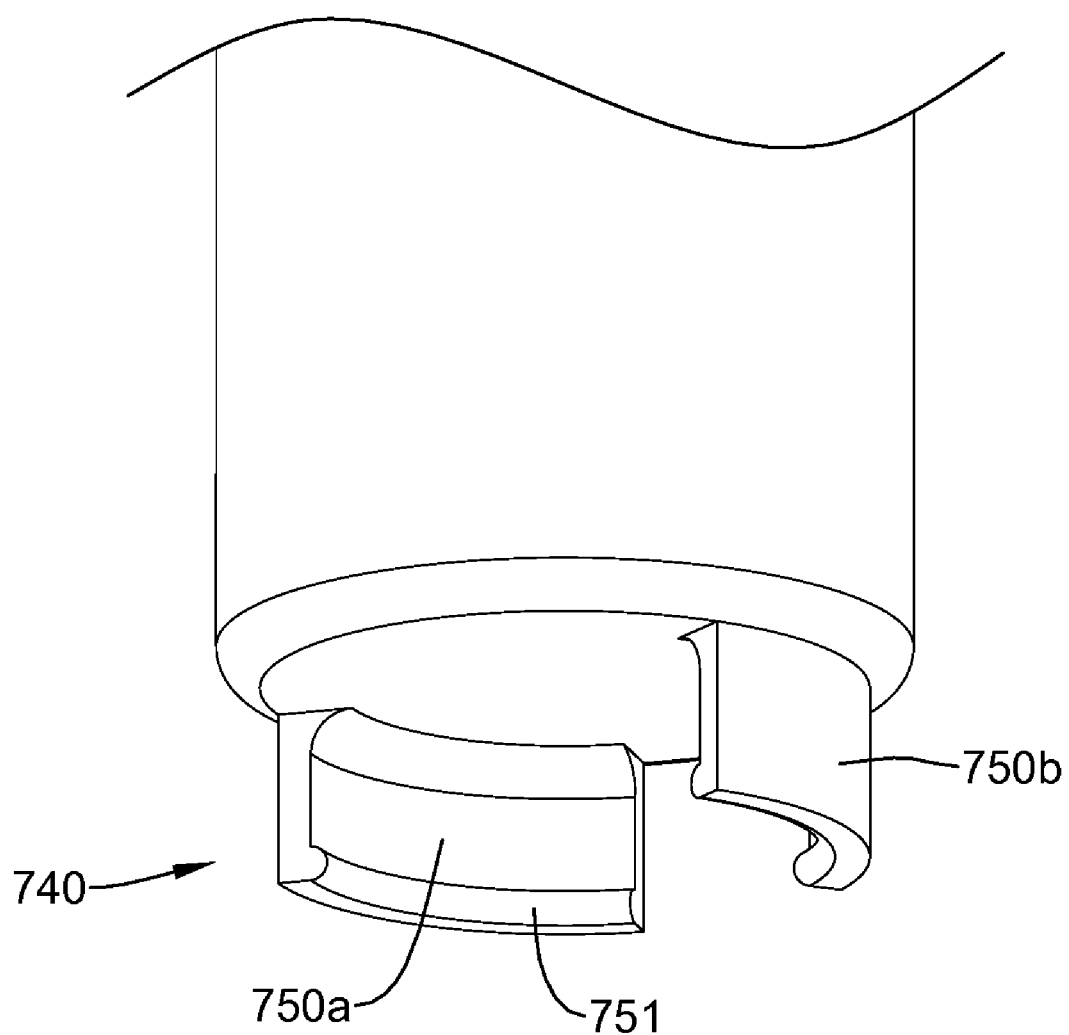
FIG. 8 is a perspective view of an example securing member.

FIGS. 8-14 illustrate some examples of securing members that may be utilized in any of the biopsy caps disclosed herein. For example, FIG. 8 illustrates securing member 740, which may be similar to securing members 140 and/or other securing members disclosed herein. Securing member 740 may include a pair of locking tabs 750a/750b that may be fitted onto and secured to port 20. Tabs 750a/750b, which may be similar to tabs 150a/150b, may be configured to snap onto port 20. In some embodiments, tabs 750a/750b may include a ridge 751. Ridge 751 may help to hold securing member 740 onto port 20 and/or mate with another ridge 751 or groove that may be formed on port 20.

Figure 9:
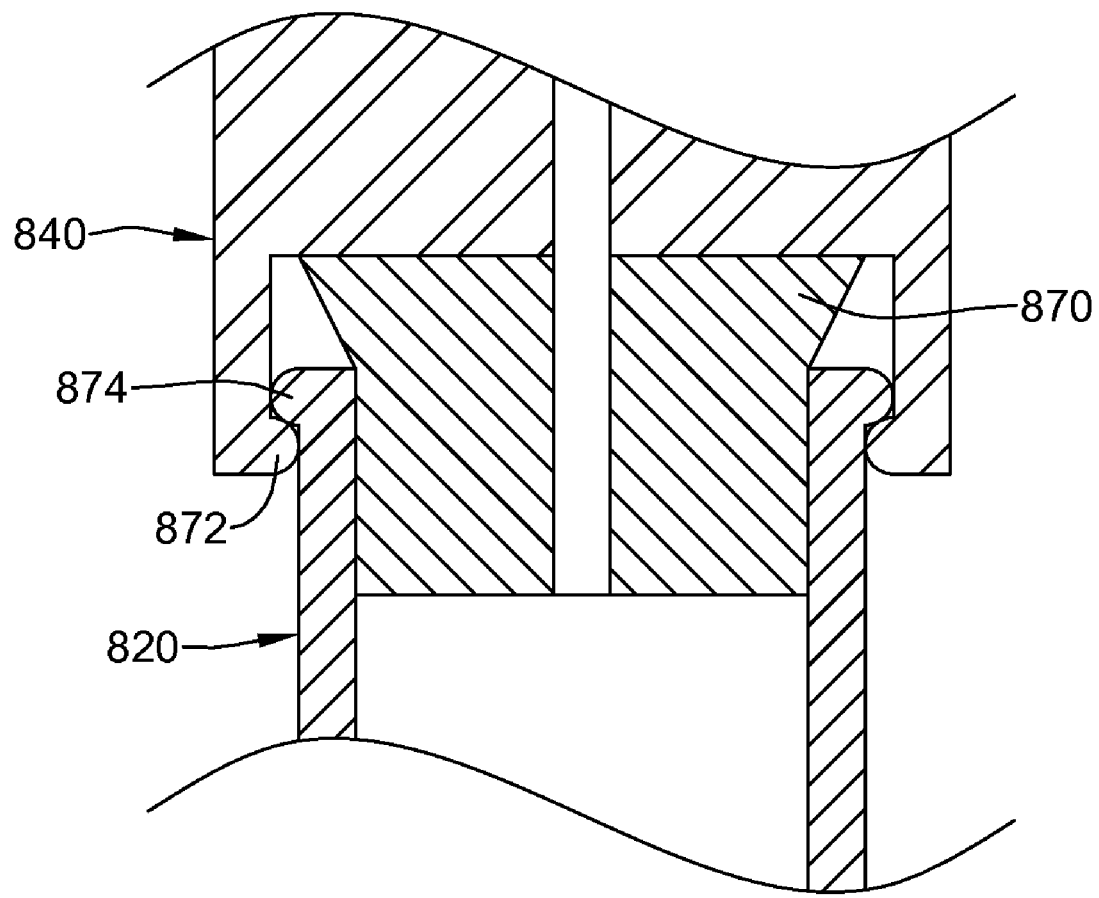
FIG. 9 is a perspective view of another example securing member.

FIG. 9 illustrates another example securing member 840, which may be utilized in conjunction with any of the caps disclosed herein. Securing member 840 may include a plug or stopper 870 that may be configured to fit within port 820 in a manner similar to a cork or rubber stopper. Indeed, plug 870 may be made from similar materials including, for example, cork, rubber, and the like or other suitable sealing materials. In addition, securing member 840 may also include a ridge 872 that helps to hold securing member 840 in place, for example, adjacent a ridge 874 formed on the end of port 820. Alternatively, port 820 may include a groove (not shown) that is configured to mate with ridge 872.

Figure 10:
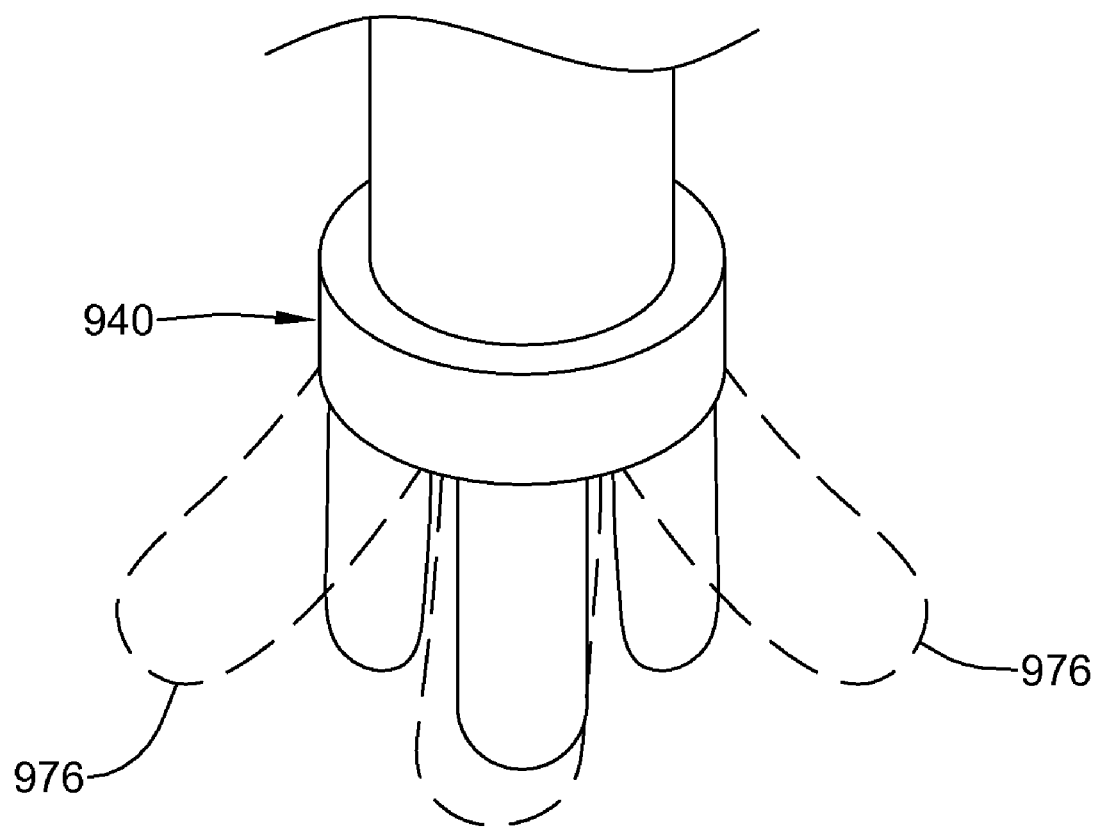
FIG. 10 is a perspective view of another example securing member.

FIG. 10 illustrates another example securing member 940. Securing member 940 may include a plurality of leaf-like fingers 976. Fingers 976 may be configured to shift between a first or "open" position (depicted in phantom) and a second or "closed" position, the later being used to hold securing member 940 onto an access port. In some embodiments, fingers 976 may grasp onto or hold onto a side portion of the access port and/or the endoscope. Alternatively, fingers 976 may wrap around (e.g., the back side of) the access port and/or endoscope.

In at least some embodiments, fingers 976 are made from a deformable material that allows them to shift between the first and second positions and hold the desired shape/position. Leaf-like fingers 976 may be utilized alone as a securing member 940, as shown, or as a secondary attachment means by combining them with other securing members 940.

Figure 11A:
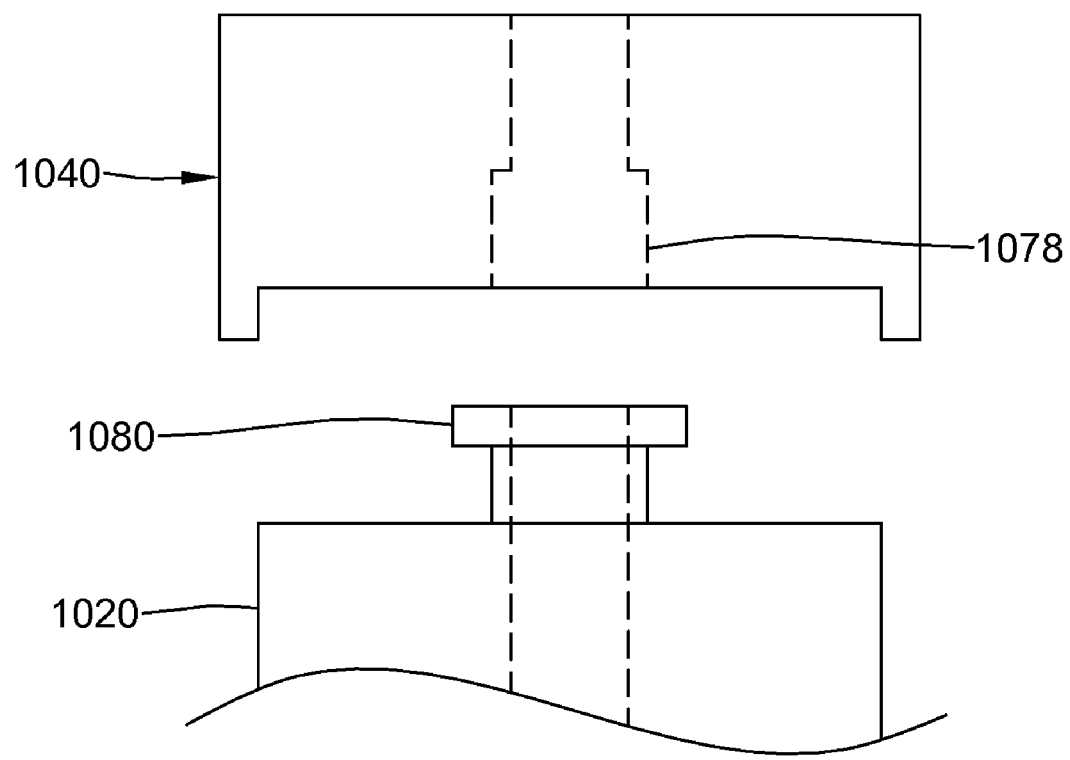
FIG. 11A is a perspective view of another example securing member in a first configuration.
Figure 11B:
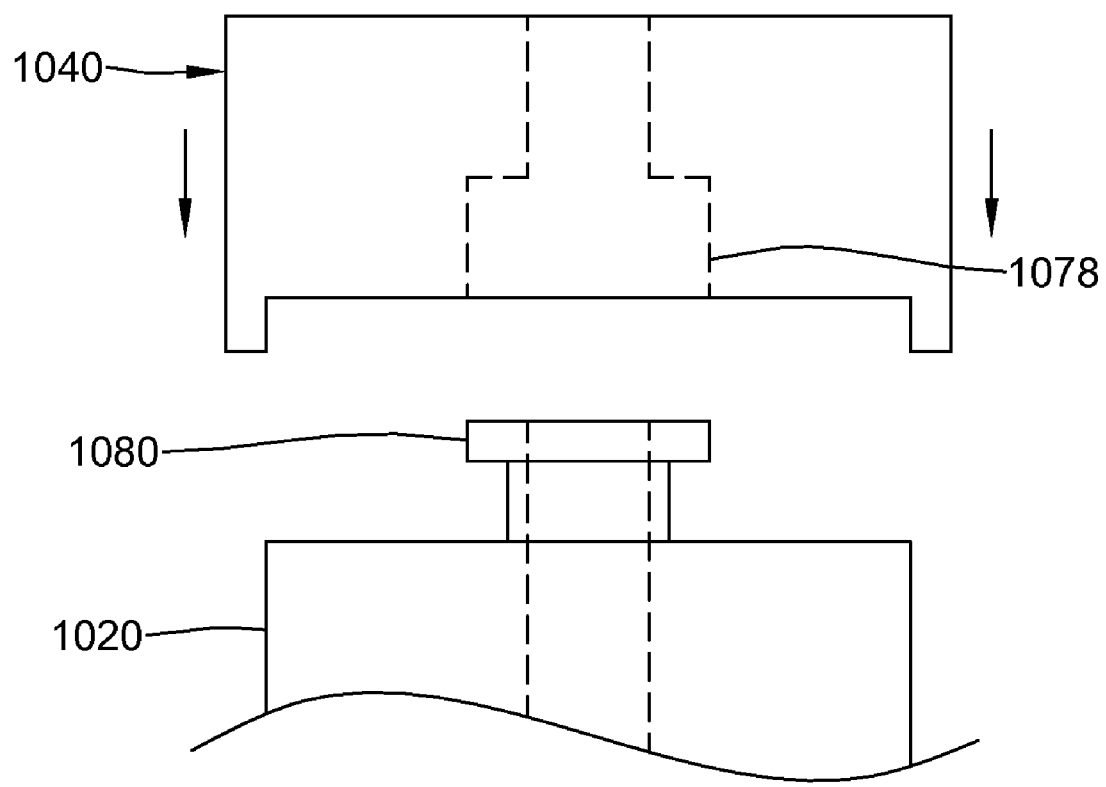
FIG. 11B is a perspective view of the example securing member illustrated in FIG. 11A in a second configuration.

FIGS. 11A and 11B illustrate another example securing member 1040. Securing member 1040 may include an end with a deformable or flexible opening 1078 that is configured to shift between a narrowed configuration (illustrated in FIG. 11A) and an expanded configuration (illustrated in FIG. 11B). When in the expanded configuration, opening 1078 may be fitted over a portion of port 1020, for example, such as a flange or ridge 1080 on port 1020. Shifting may be accomplished by the nature of the material in which opening 1078 is formed. For example, the end of securing member 1040 may include a flexible polymer, rubber, and the like, or any other suitable material that may be resilient enough to undergo the necessary shifts in size. Once seated, opening 1078 may shift or partially shift back to the narrowed configuration and seal about port 1020.

Figure 12:
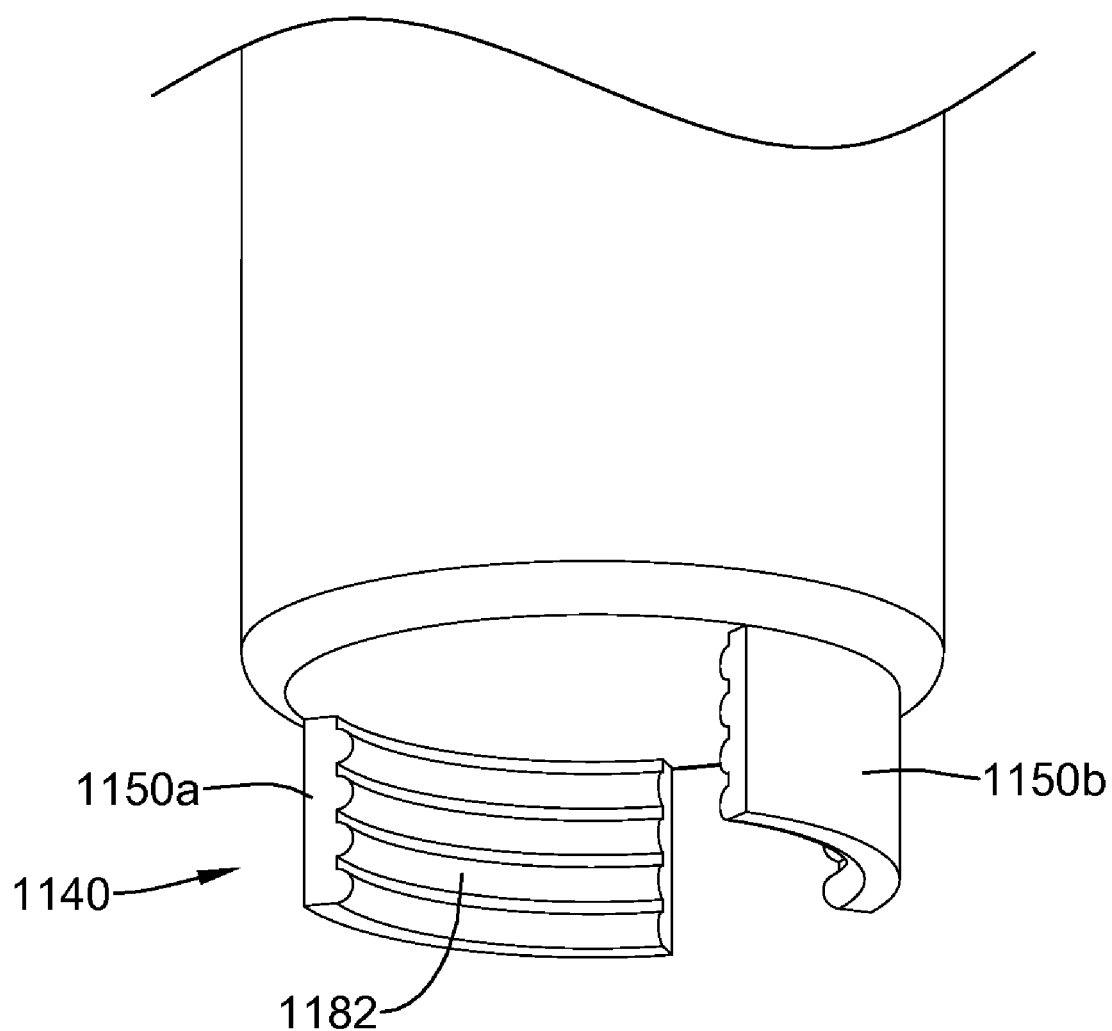
FIG. 12 is a perspective view of another example securing member.

FIG. 12 illustrates another example securing member 1140 that may be similar in form and function to other securing members disclosed herein. Securing member 1140 may include a plurality of tabs 1150a/1150b having threads 1182 formed thereon. Other than having threads 1182 formed thereon, tabs 1150a/1150b may be similar to tabs 150a/150b and/or tabs 750a/750b. Securing member 1140 may be configured to attach to an access port by threading onto the port (e.g., port 20 or a version of port 20 with corresponding threads).

Figure 13:
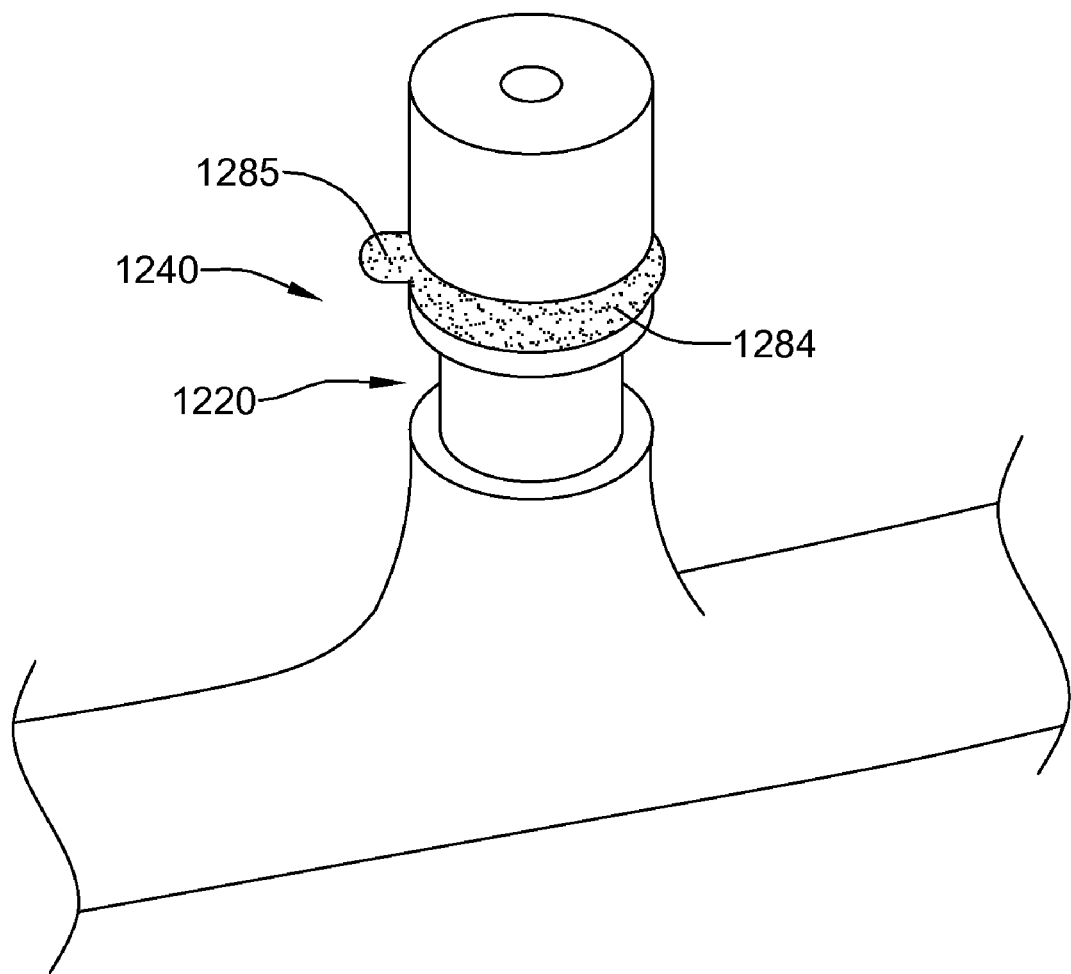
FIG. 13 is a perspective view of another example securing member.

FIG. 13 illustrates another example securing member 1240 that may be similar in form and function to other securing members disclosed herein. Securing member 1240 may include a "quick release" pull tab 1284. Tab 1284 may be disposed on the end of port 1220. In some embodiments, tab 1284 may include an adhesive that is configured to form a seal at port 1220 and thus hold the biopsy cap onto port 1220. In addition, the adhesive in tab 1284 may be disrupted or pulled thereon, for example at a pull point 1285, so that the cap can be quickly and easily removed from port 1220, as desired.

FIGS. 14A-19 illustrate example locking members that may be utilized with any of the biopsy caps disclosed herein. These locking members may be attached to a biopsy cap at any suitable position thereon and they may be used to secure the position of a medical device (e.g., a guidewire, catheter, etc.) relative to the cap (and/or endoscope 10). Just like was the case for the securing members disclosed above, some of the additional cap structure is omitted from FIGS. 14A-19 for simplicity purposes. However, it can be appreciated that any of the locking members shown and contemplated may be attached to a biopsy cap using conventional methods to achieve the desired result.

Figure 14A:
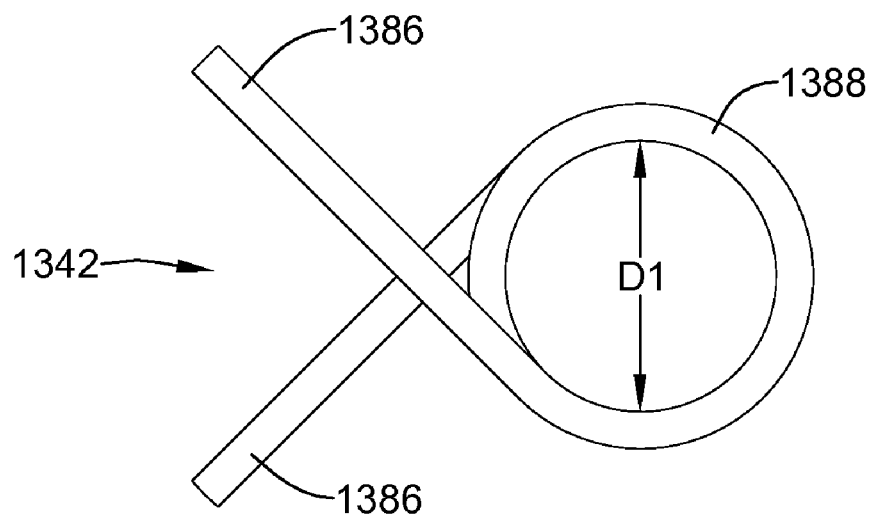
FIG. 14A is a perspective view of an example locking member in a first configuration.
Figure 14B:
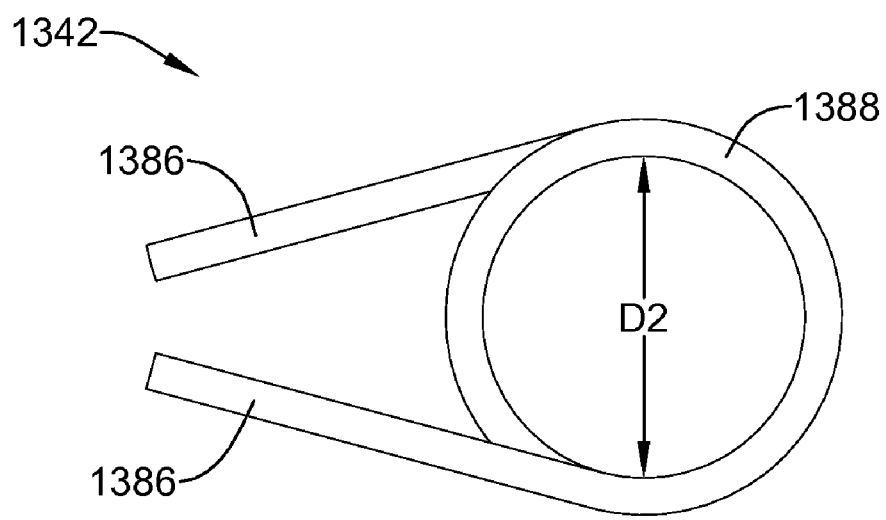
FIG. 14B is a perspective view of the example locking member illustrated in FIG. 14A in a second configuration.

FIGS. 14A and 14B illustrate locking member 1342, which may be configured to shift between a first configuration (as illustrated in FIG. 14A) and a second configuration (as illustrated in FIG. 14B). Locking member 1342 may include a pair of actuating arms 1386 that, when actuated, shift a locking ring 1388 from the first or smaller configuration that defines a smaller diameter D1 to the second or larger configuration that defines a larger diameter D2. Locking member 1342 may be described as being a spring clip or spring wing as locking ring 1388 may include a plurality of loops of material with a spring-like configuration. The extra portion or loops of the "spring" may be utilized to accommodate the expansion in size of ring 1388. In at least some embodiments, locking member 1342 may have a form similar to a clip that may be used to secure weights onto a barbell.

Although not shown, locking member 1342 may be attached to a biopsy cap at any suitable location using any suitable means. For example, a portion of arms 1386 and/or ring 1388 may be directly attached to a cap. Alternatively, an arm or member may extend from the cap that attaches to locking member 1342. In still other embodiments, locking member 1342 may include an additional structure such as a clip to removably secure locking member 1342 to a cap. These later embodiments of locking member 1342 and other locking members may be desirable because they may allow different types of locking members to be "mixed and matched" based on their particular applicability to a given intervention.

Figure 15:
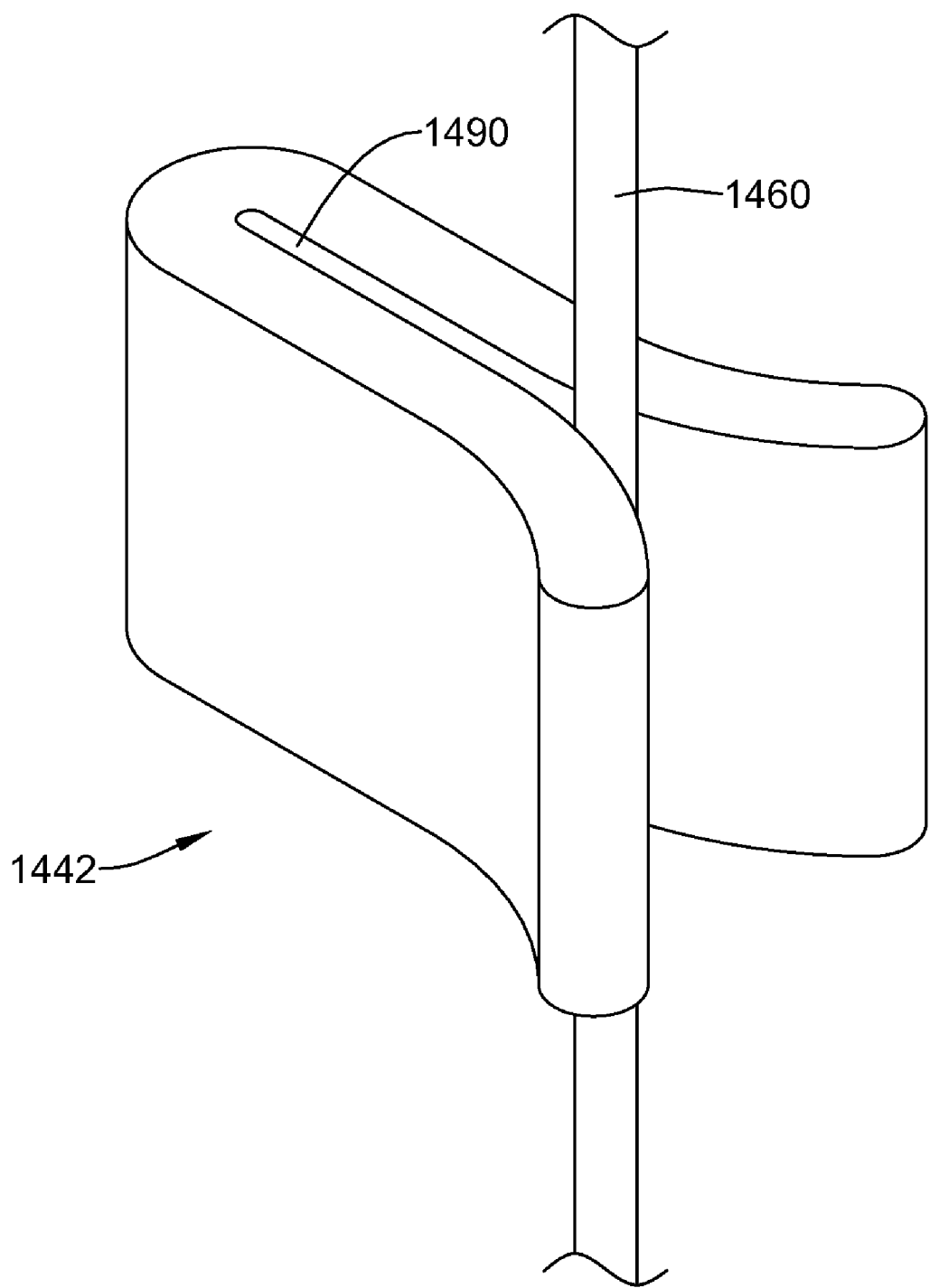
FIG. 15 is a perspective view of another example locking member.

FIG. 15 illustrates another example locking member 1442, which may be used with any of the biopsy caps disclosed herein. Locking member 1442 may have a wedge-like shape and may have a channel or groove 1490 formed therein where device 1460 (e.g., a guidewire, catheter, etc.) can be disposed therein and held by friction. Just like the other locking members disclosed herein, locking member 1442 may be attached to a biopsy cap at any suitable location using any suitable means.

Figure 16A:
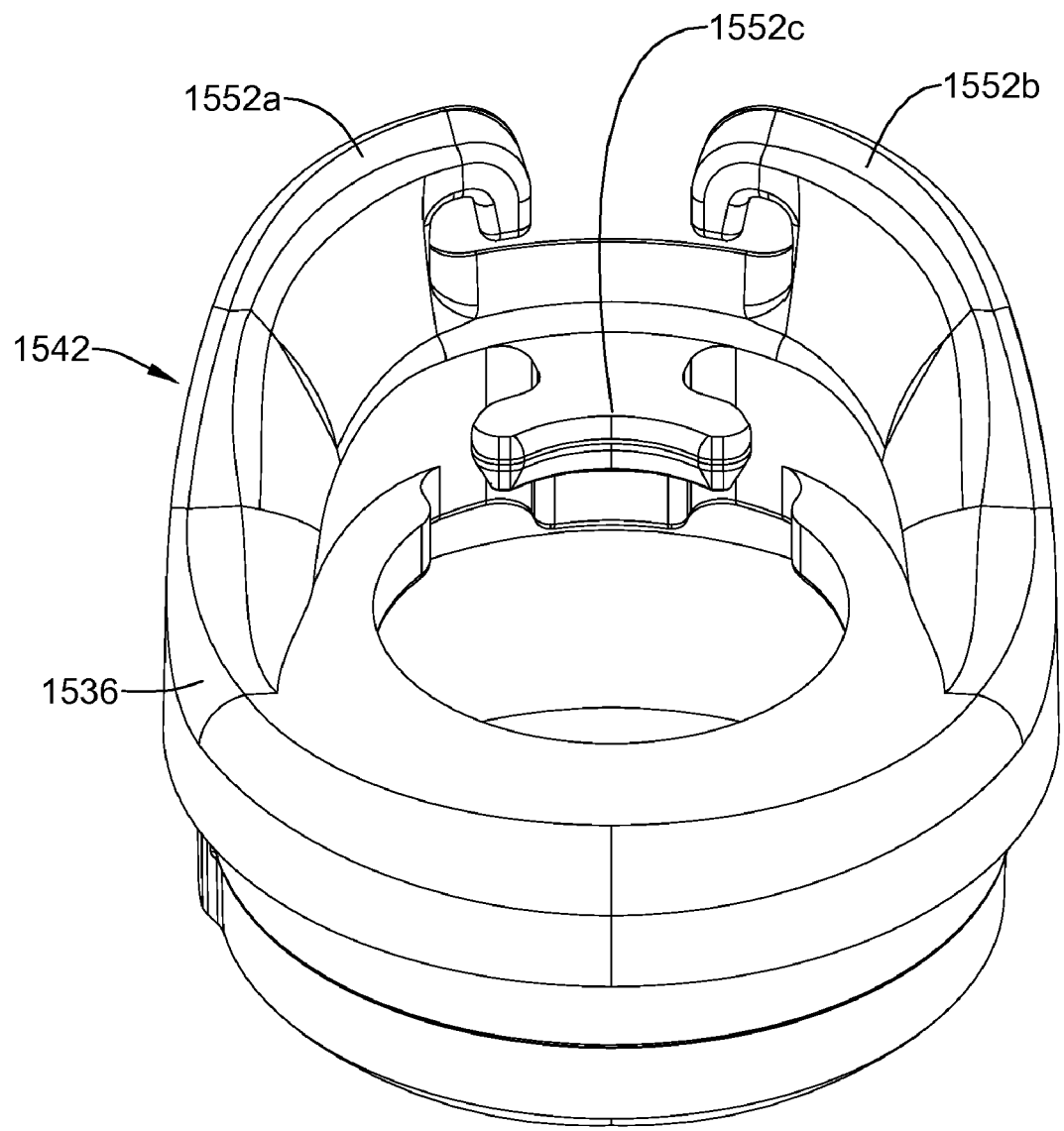
FIG. 16A is a perspective view of another example locking member.

FIG. 16A illustrates another example locking member or locking assembly 1542, which may be used with any of the biopsy caps disclosed herein. Locking member 1542 may include a plurality of locking features including, for example, a pair of arms 1552a/1552b that are coupled to or integrally formed on shell 1536. Arms 1552a/1552b may be shaped in a manner that may allow them to secure the position of a device (e.g., a guidewire, catheter, etc.). For example, arms 1552a/1552b may include one or more bends, hooks, grooves, and/or the like. Locking member 1542 may also include another locking structure or arm 1552c that may be disposed below arms 1552a/1552b. By virtue of having this position, arm 1552c may be used in conjunction with one or more of arms 1552a/1552b to allow the device to be wrapped around the desired combination of structures 1552a/1552b/1552c.

Figure 16B:
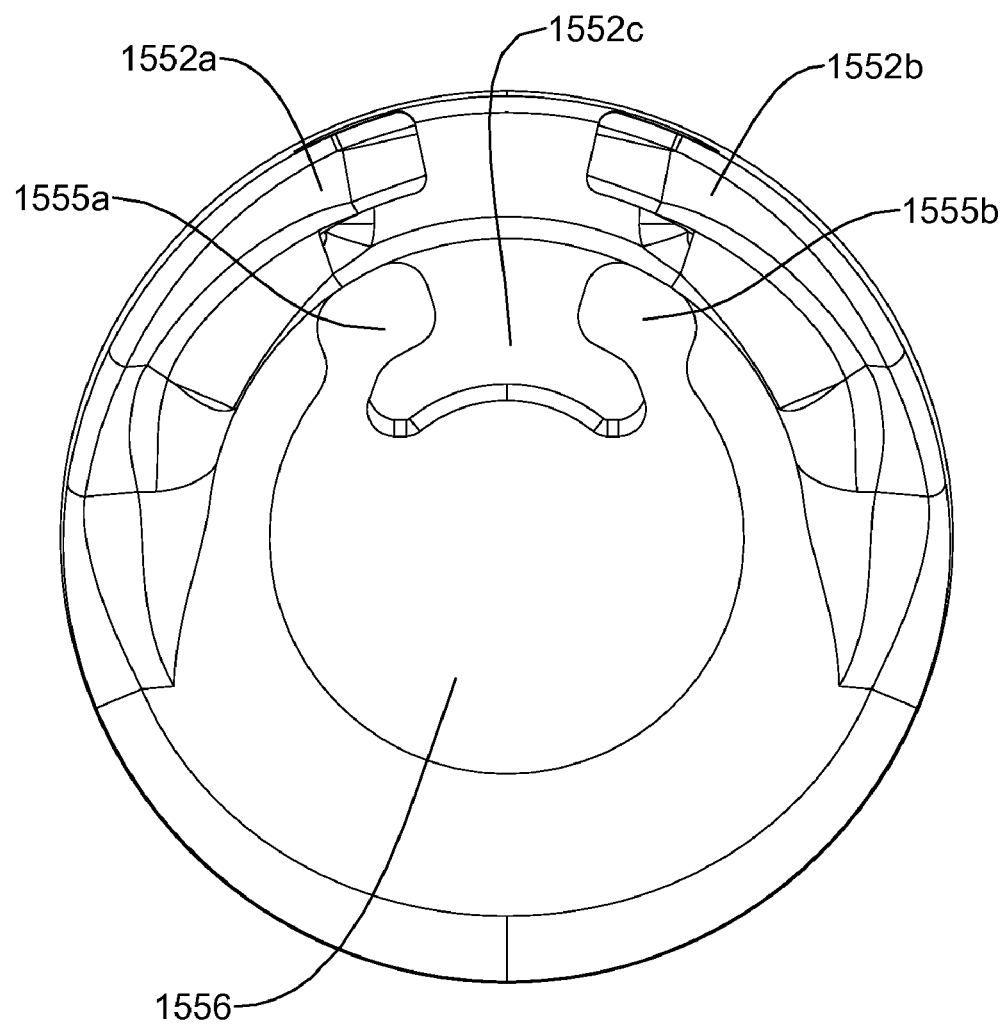
FIG. 16B is a perspective view of an alternative locking member to that depicted in FIG. 16A.

As illustrated in FIG. 16B, which is a rotated view of the locking member 1542 of FIG. 16A, the arm 1552c is shaped to create slotted openings 1555a/1555b in cooperation with the opening 1556 in the upper end of the shell. In some embodiments, the slotted opening is shaped with a narrowed opening which expands into a larger instrument holding area that has contoured surfaces for easy placement and removal of an instrument.

Figure 16C:
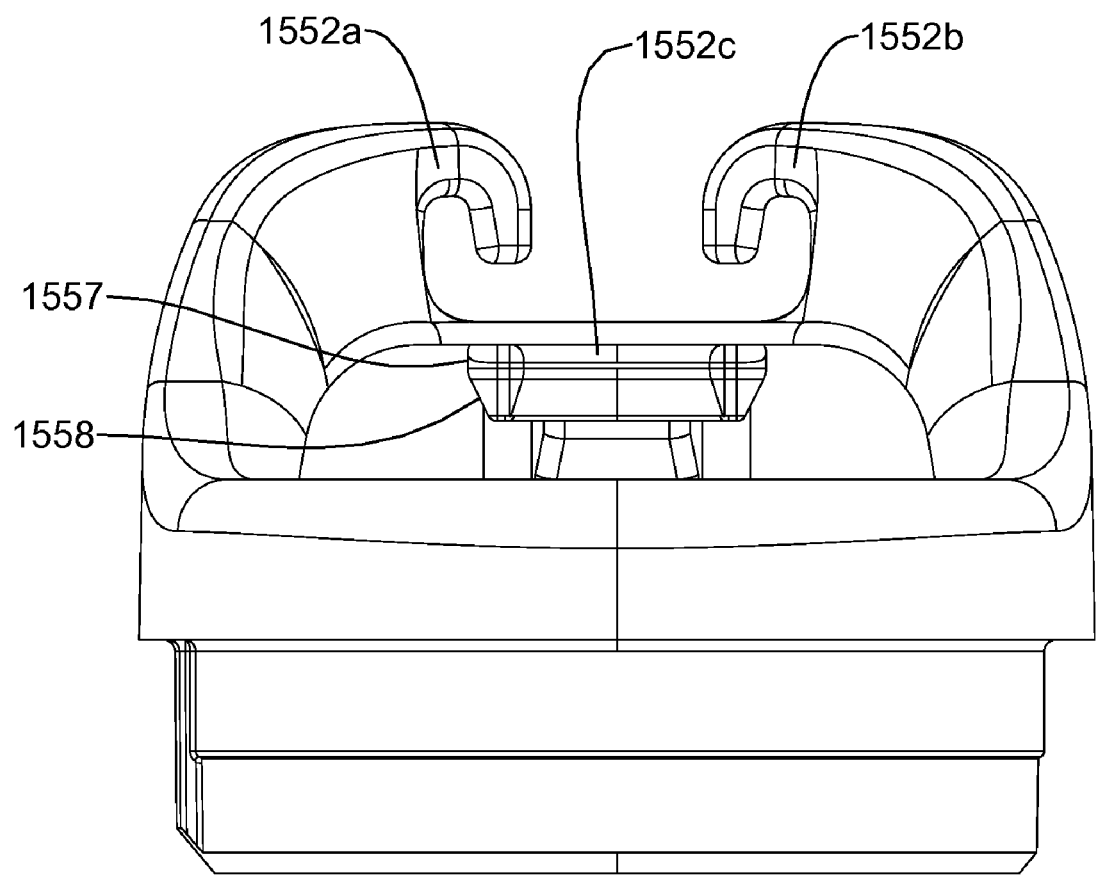
FIG. 16C is a perspective view of the alternative locking member of FIG. 16B showing further details.

FIG. 16C provides further detail of an exemplary design of arm 1552c. As indicated, the surface of arm 1552c is contoured to provide easy movement of a guidewire or instrument around its surface. Further, the edge 1557 includes an open shoulder 1558 along the lower portion of the lateral surface of arm 1552c. This surface helps prevent instruments from catching on arm 1552c.

Figure 17:
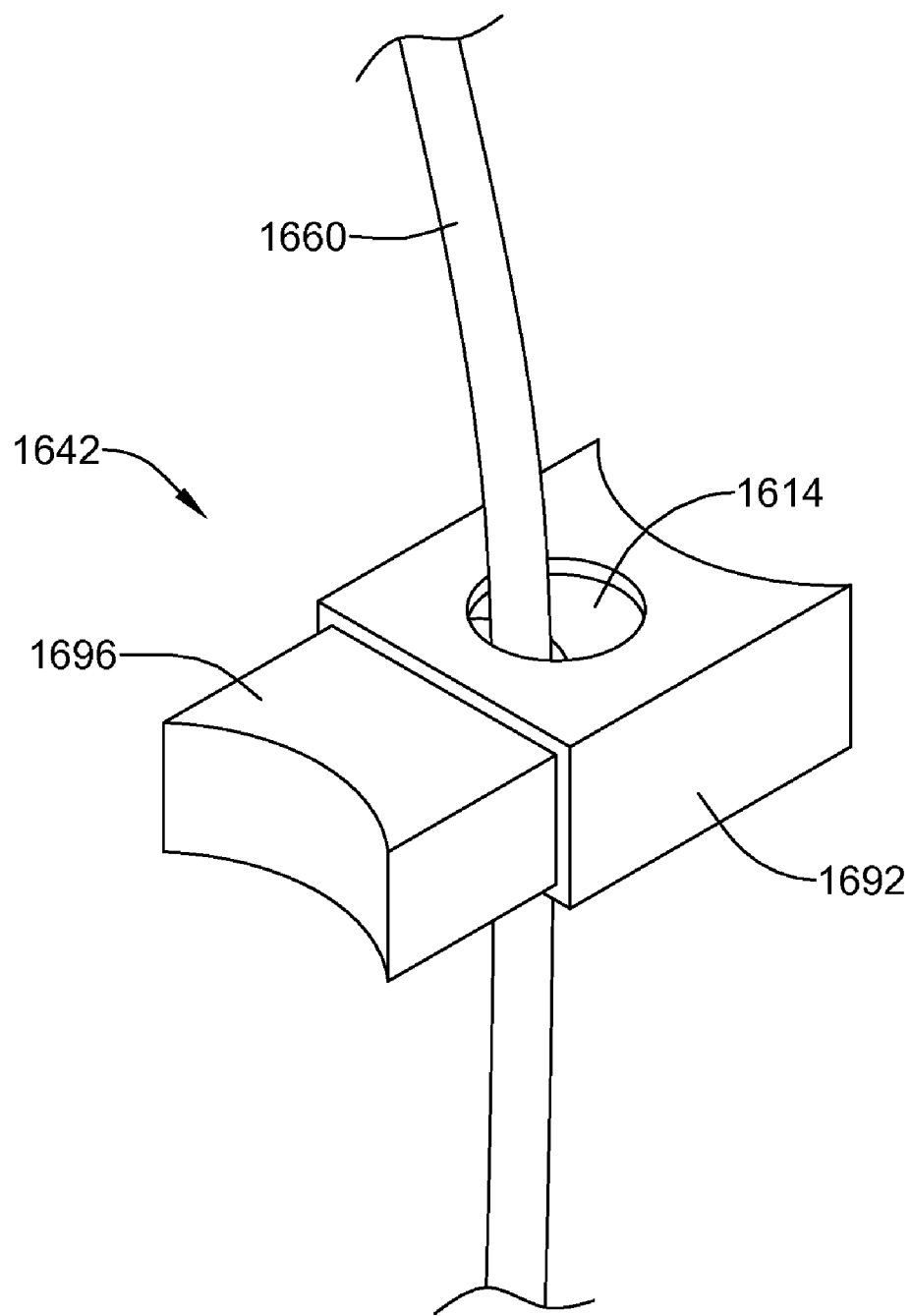
FIG. 17 is a perspective view of another example locking member.

FIG. 17 illustrates another example locking member 1642, which may be used with any of the biopsy caps disclosed herein. Locking member 1642 may include a base 1692 having an opening 1614 formed therein. Device 1660 may extend through opening 1614. A spring button 1696 may be attached to base 1692. Spring button 1696 may be coupled to a spring (not shown) that biases a portion of button 1696 (e.g., a rear portion of button 1696 that may be disposed within base 1692 on the opposite side of opening 1614) into opening 1614, thereby "closing" or "locking" opening 1614. Depressing button 1696 may overcome the bias and open opening 1614 so that device 1660 can be extended therethrough. Releasing button 1696 allows the spring to press button 1696 back into the biased position and lock the position of device 1660.

A number of different configurations are contemplated for locking member 1642. For example, locking member 1642 may have a barrel-like or cylindrical shape rather than the more squared or rectangular shape as shown. In addition, locking member 1642 may include a lock that can reversibly hold button 1696 in the desired position such as, for example, the locked position.

Figure 18:
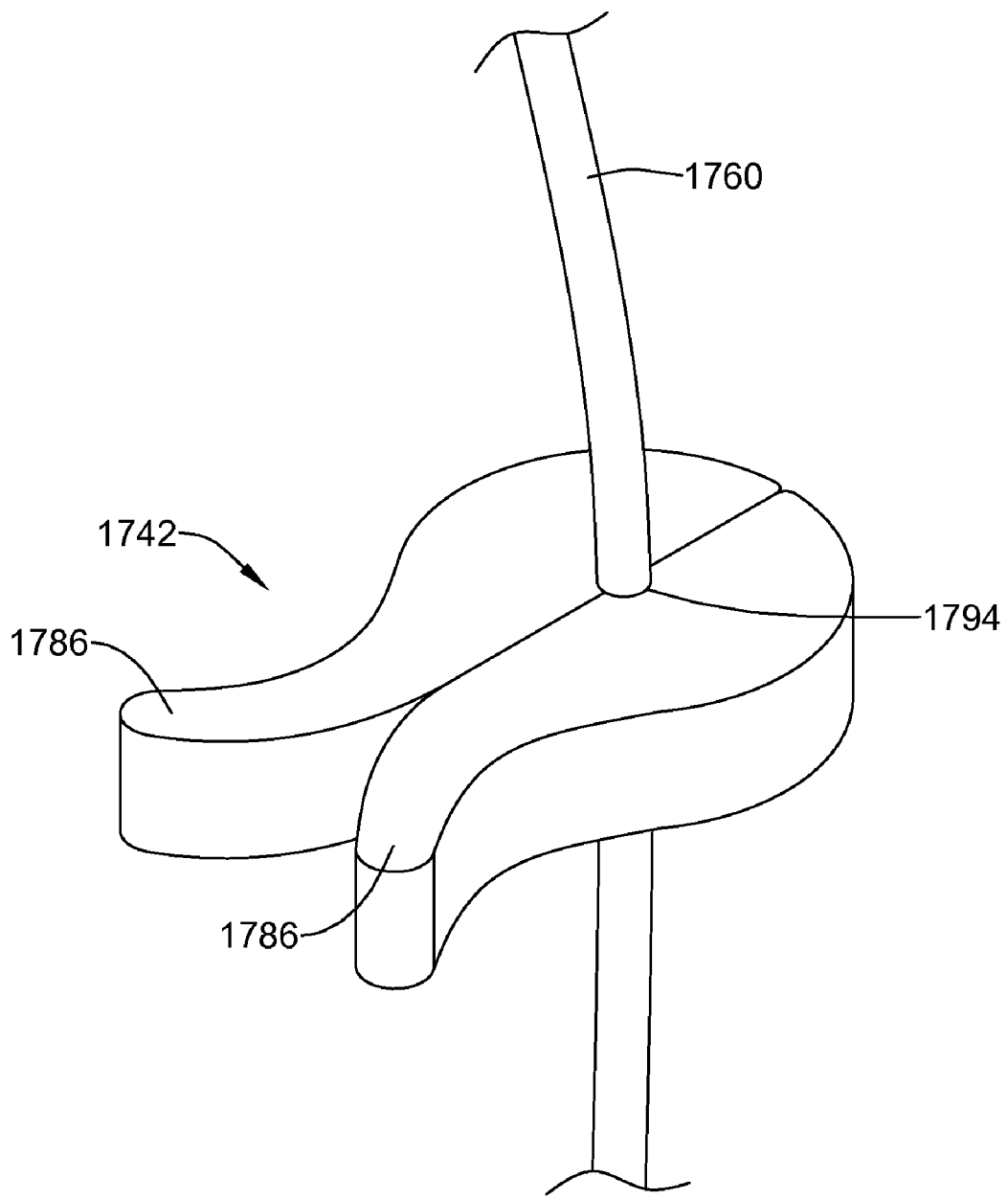
FIG. 18 is a perspective view of another example locking member.

FIG. 18 illustrates another example locking member 1742, which may be used with any of the biopsy caps disclosed herein. Locking member 1742 may include a pair of arms 1786 that can be actuated to open/close opening 1794 to secure device 1760. Locking member 1742 may function in a manner similar to a clothespin. As such, locking member 1742 may include a spring or other biasing member (not shown) that holds it in either the open (e.g., "unlocked") or closed (e.g., "locked") positions.

Figure 19:
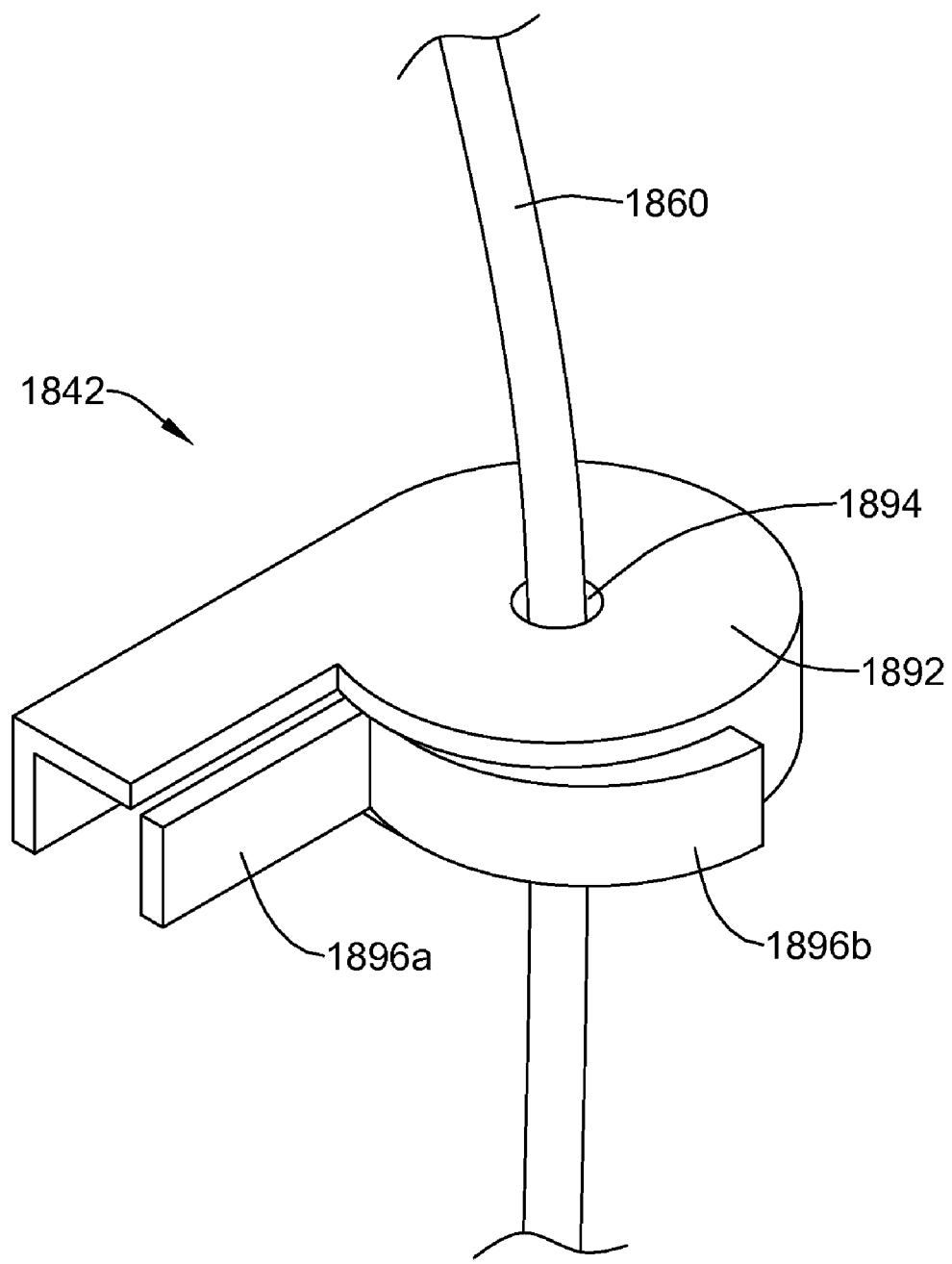
FIG. 19 is a perspective view of another example locking member.

FIG. 19 illustrates another example locking member 1842, which may be used with any of the biopsy caps disclosed herein. Locking member 1842 may include a base 1892 having opening 1894 formed therein. Device 1860 may extend therethrough. A pair of buttons 1896a/1896b may be attached to base 1892 for opening/closing opening 1894. For example, one of the buttons (e.g., button 1896b) may be depressed to "lock" device 1860 while the other button (e.g., button 1896a) may be depressed to open or "unlock" device 1860.

Figure 20A:
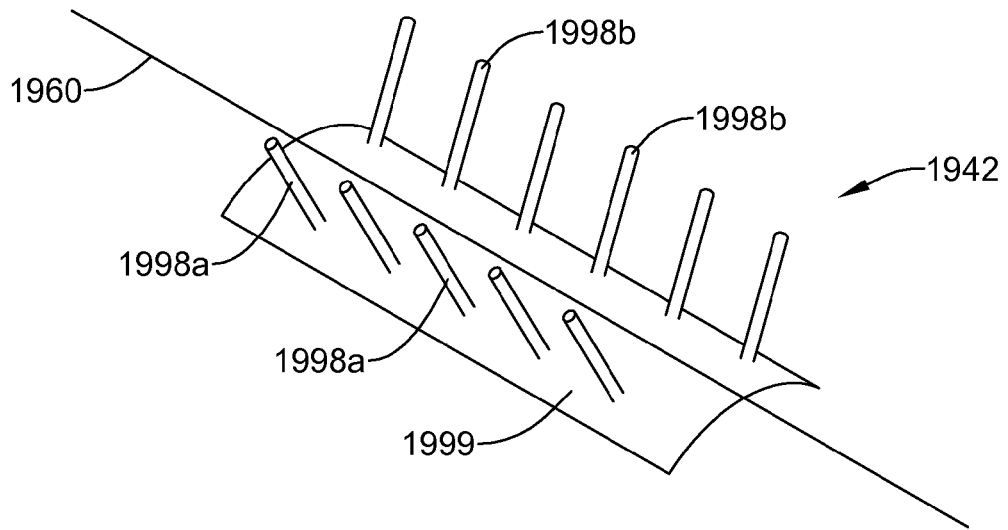
FIG. 20A is a perspective view of another example locking member in a first configuration.
Figure 20B:
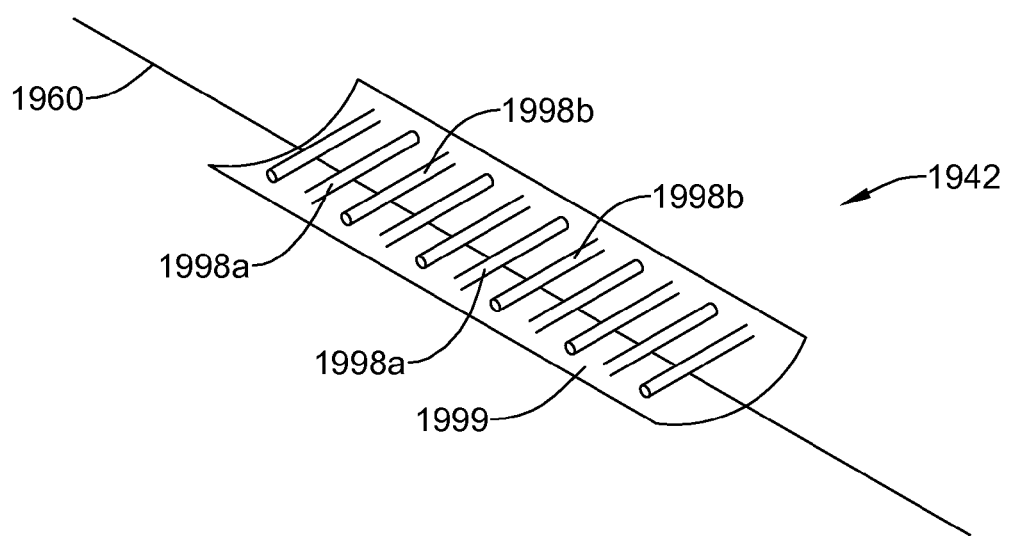
FIG. 20B is a perspective view of the example locking member illustrated in FIG. 20A in a second configuration.
Figure 21A:
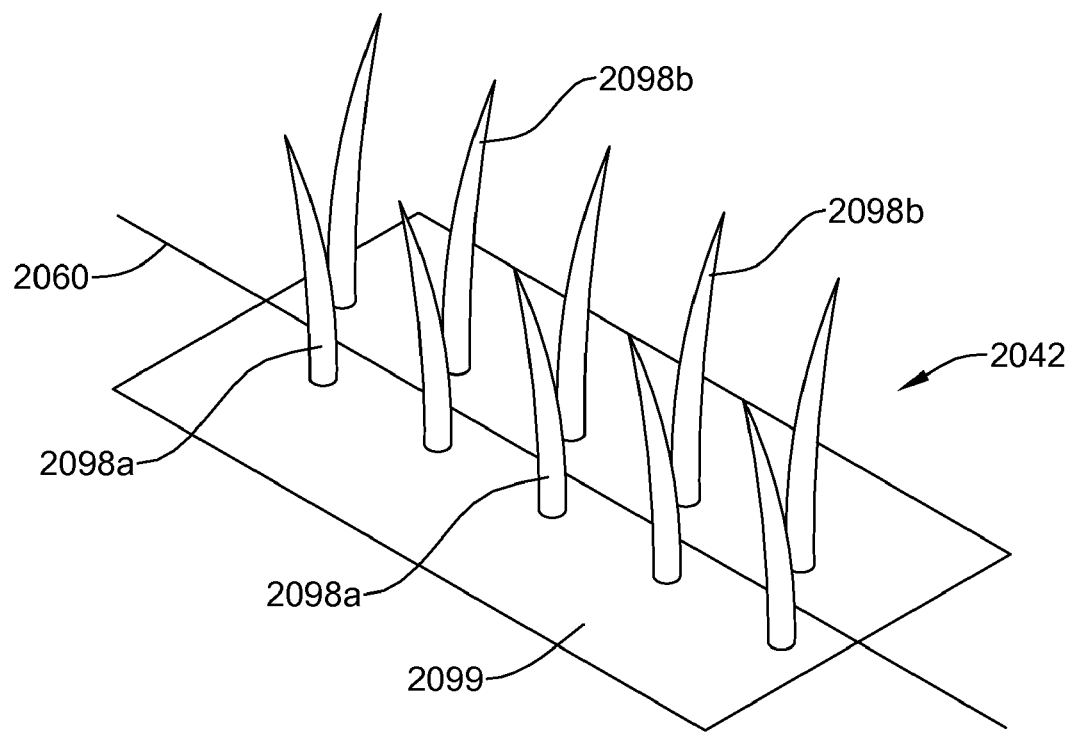
FIG. 21A is a perspective view of another example locking member in a first configuration.
Figure 21B:
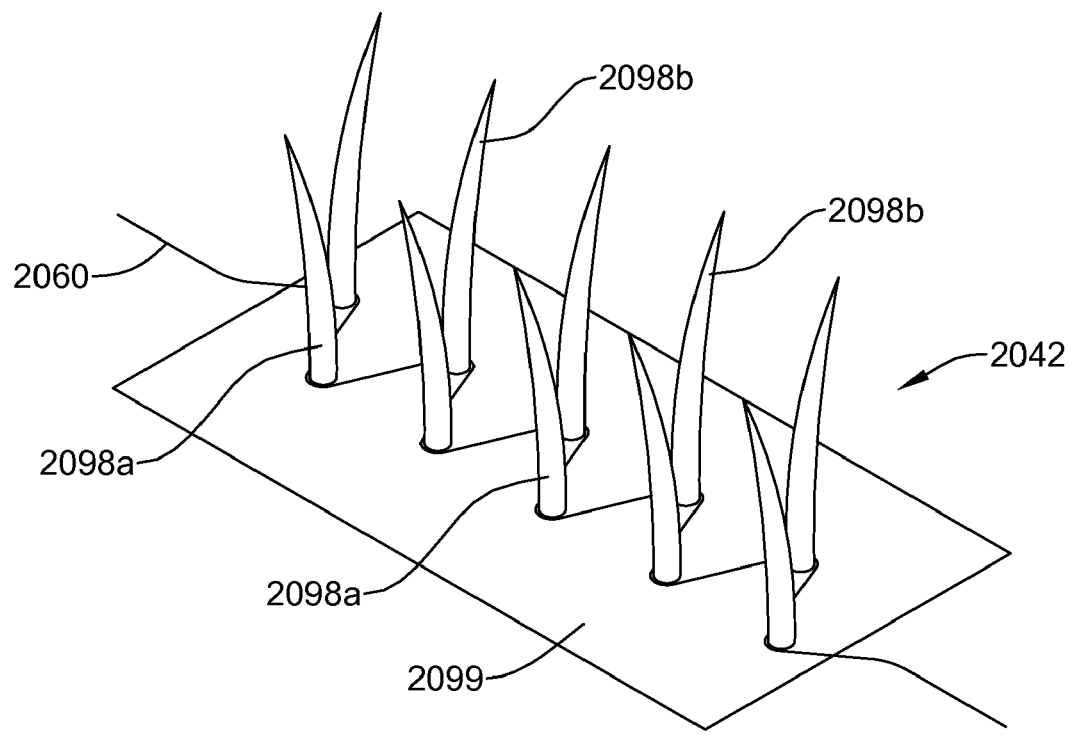
FIG. 21B is a perspective view of the example locking member illustrated in FIG. 21A in a second configuration.

FIGS. 20A and 20B illustrate locking member 1942, which may be configured to shift between a first or open configuration (as illustrated in FIG. 20A) and a second or closed configuration (as illustrated in FIG. 20B). Locking member 1942 may include a pair of opposing sets of fingers 1998a/1998b coupled to a base 1999 that are configured to shift from the upright or open first position to the horizontal or flat second configuration, the later being configured to secure the position of device 1960. FIGS. 21A and 21B illustrate locking member 2042, which may be similar in form and function to locking member 1942. Locking member 2042 may include a pair of opposing sets of fingers 2098a/2098b coupled to a base 2099. Device 2060 may extend through fingers 2098a/2098b as shown in FIG. 21A, which may hold device 2060 in place, for example, by friction. Alternatively, device 2060 may be wrapped around fingers 2098a/2098b, as shown in FIG. 21B.

Base 1999/2099 of locking members 1942/2042 may desirably add a surface substrate that may allow these devices to be attached to a biopsy cap. In some embodiments, base 1999/2099 may include a strip of polymer or plastic that can be bonded to a biopsy cap with a permanent adhesive. In other embodiments, base 1999/2099 may be configured to be removably attached to the biopsy cap. For example, a removable or temporary adhesive may be used, base 1999/2099 may be "velcroed" onto the cap, etc.

Figure 22A:
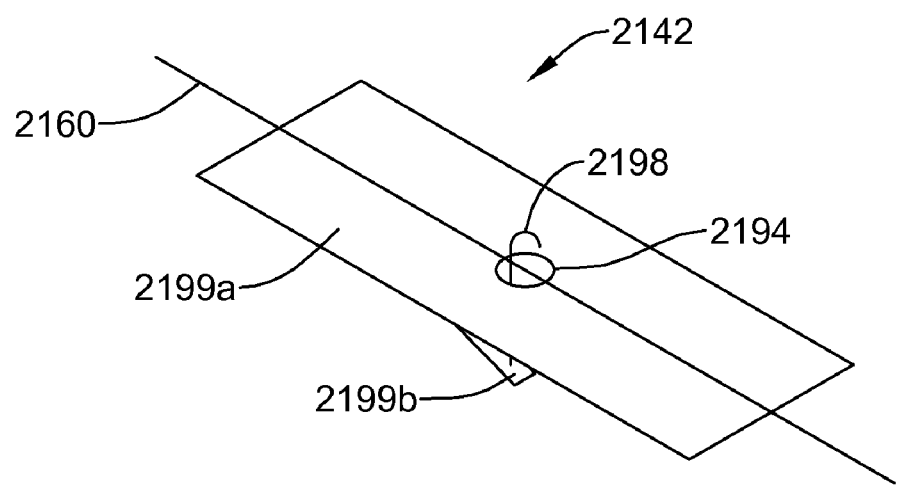
FIG. 22A is a perspective view of another example locking member in a first configuration.
Figure 22B:
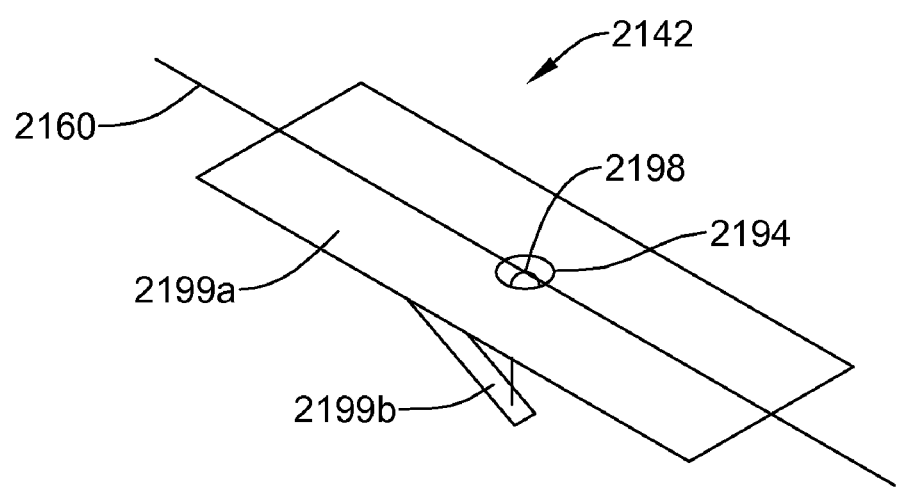
FIG. 22B is a perspective view of the example locking member illustrated in FIG. 22A in a second configuration.

FIGS. 22A and 22B illustrate locking member 2142, which may be configured to shift between a first configuration (as illustrated in FIG. 22A) and a second configuration (as illustrated in FIG. 22B). Locking member 2142 may include a base 2199a including a platform region 2199b. Region 2199b may include a hook-like extension 2198 that extends through an opening 2194 in base 2199a and that can grasp device 2160 when actuated (as illustrated in FIG. 22A). Region 2199b may be hingedly connected to base 2199a so that region 2199b can be moved up or down, as desired, to engage device 2160.

Figure 23:
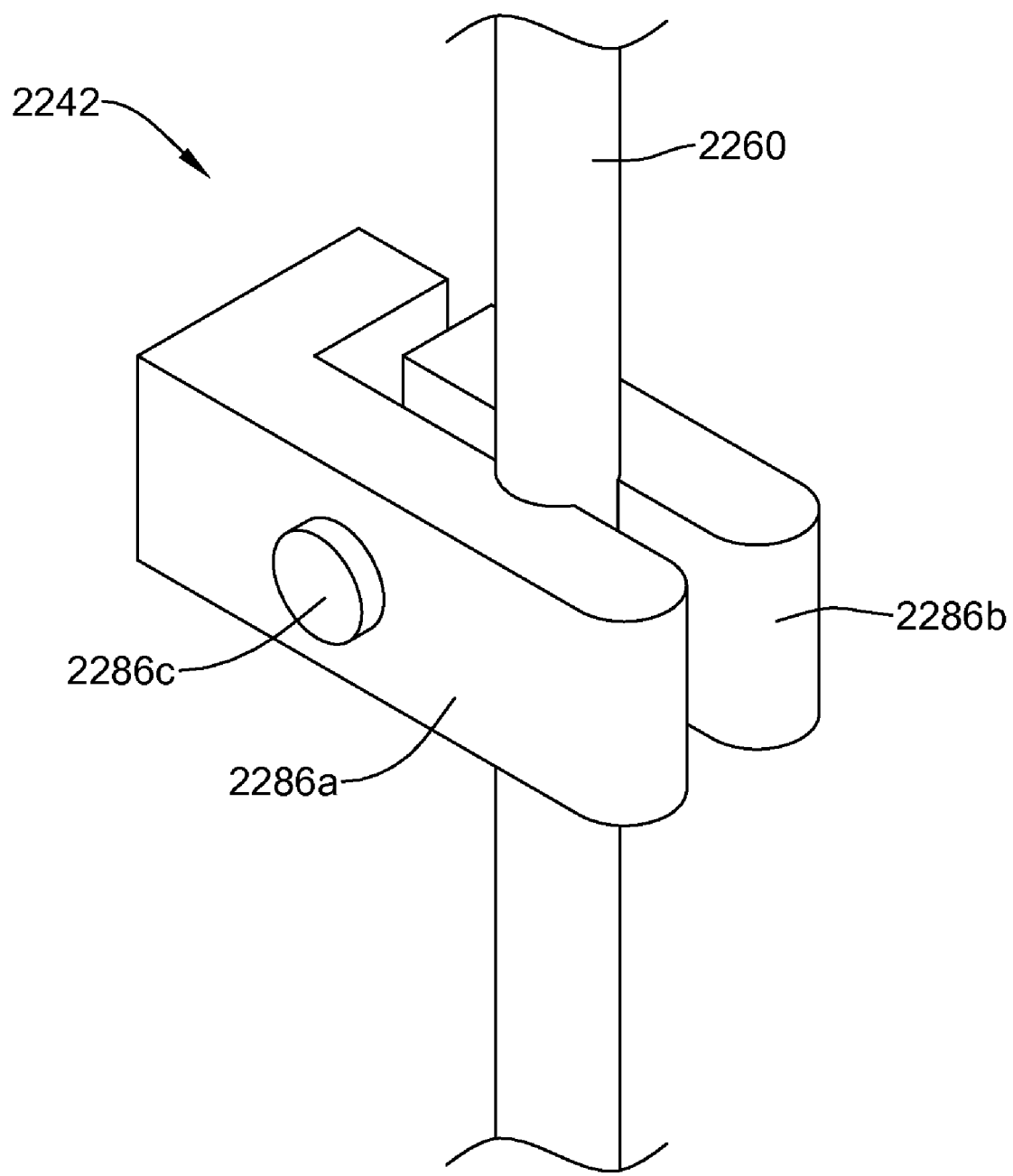
FIG. 23 is a perspective view of another example locking member.

FIG. 23 illustrates another example locking device 2260, which may be used with any of the biopsy caps disclosed herein. Device 2260 may include a pair of arm segments 2286a/2286b coupled together by a linkage 2286c. Linkage 2286c may be slidable within one of the arm segments 2286a/2286b so that arms 2286a/2286b can be brought into closer contact with one another by pinching together arms 2286a/2286b and locking the position of device 2260. Manually moving arms 2286a/2286b further apart may release device 2260.

In some embodiments, one or more additional locking members may be added to a cap. The additional locking member may take any suitable form including any of those disclosed herein. Adding the locking members may include fastening, snapping on, or hingedly connecting an external locking member assembly onto the cap. Some additional discussion of wire or other locking devices which may be suitable for use with a biopsy cap may include U.S. Patent Application Pub Nos. US2006/0229496A1, US2005/0148820A1, and US2004/0106852A1 as well as U.S. Pat. Nos. 7,060,052, 7,037,293, 6,893,393, 6,663,597, and 6,096,009, the entire disclosures of which are herein incorporated by reference.

The various caps as well as the various components thereof may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In at least some embodiments, portions or all of the structures disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of endoscope 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of endoscope 10 or the various components thereof to achieve the same result.

In some embodiments, a degree of MRI compatibility may be imparted into the structures disclosed herein. For example, to enhance compatibility with Magnetic Resonance Imaging (MRI) machines, it may be desirable to make a portion of endoscope 10 in a manner that would impart a degree of MRI compatibility. For example, a portion of endoscope 10 may be made of a material that does not substantially distort the image and create substantial artifacts (artifacts are gaps in the image). Certain ferromagnetic materials, for example, may not be suitable because they may create artifacts in an MRI image. A portion of endoscope 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. An endoscope biopsy cap, comprising:
   an outer shell having an opening formed therein and a base, the outer shell including threads formed thereon;
   a locking member coupled to the outer shell for securing the position of a medical device disposed in the opening;
   an inner seal member disposed within the outer shell; and
   an actuator coupled to the base for shifting the inner seal member between an unsealed configuration and a sealed configuration;
   wherein the actuator includes a rotatable ring member, the rotatable ring member including threads formed thereon, the rotatable ring member being threadably coupled to the outer shell.
2. The cap of claim 1, wherein the inner seal member includes a first seal region and a second seal region, wherein the first seal region is configured to seal against the port, and wherein the second seal region is configured to seal against a device extending through the inner seal member.
3. An endoscope assembly, comprising:
   an endoscope having a channel formed therein and a port that provides access to the channel:
   a cap coupled to the port, the cap including:
      a base;
      an outer shell including a chuck that is configured to shift between a first position and a second position;

a locking member coupled to the shell;
an inner seal member disposed within the outer shell;
one or more openings extending through the cap and into the channel; and
an actuator coupled to an outer surface of the outer shell for shifting the inner seal member between an unsealed configuration and a sealed configuration, the actuator configured to shift the chuck between the first position and the second position; and
wherein each of the chuck and the actuator include threads by which the chuck and the actuator are threadably coupled.

* * * * *